(12) United States Patent
De Boer et al.

(10) Patent No.: US 11,241,432 B2
(45) Date of Patent: *Feb. 8, 2022

(54) METHODS OF TREATING DEPRESSION USING OREXIN-2 RECEPTOR ANTAGONISTS

(71) Applicant: Janssen Pharmaceutica NV, Beerse (BE)

(72) Inventors: Peter De Boer, Breda (NL); Justine M. Kent, Titusville, NJ (US); Wayne C. Drevets, Titusville, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/092,725

(22) Filed: Nov. 9, 2020

(65) Prior Publication Data

US 2021/0052588 A1    Feb. 25, 2021

Related U.S. Application Data

(63) Continuation of application No. 15/454,628, filed on Mar. 9, 2017, now Pat. No. 10,828,302.

(60) Provisional application No. 62/306,487, filed on Mar. 10, 2016.

(51) Int. Cl.
| | | |
|---|---|---|
| *A61K 31/506* | (2006.01) | |
| *A61K 45/06* | (2006.01) | |
| *A61K 9/00* | (2006.01) | |
| *A61K 9/20* | (2006.01) | |
| *A61K 47/38* | (2006.01) | |
| *A61K 9/10* | (2006.01) | |
| *A61K 31/53* | (2006.01) | |
| *A61K 31/50* | (2006.01) | |

(52) U.S. Cl.
CPC .......... *A61K 31/506* (2013.01); *A61K 9/0095* (2013.01); *A61K 9/10* (2013.01); *A61K 9/2018* (2013.01); *A61K 9/2027* (2013.01); *A61K 45/06* (2013.01); *A61K 47/38* (2013.01); *A61K 31/50* (2013.01); *A61K 31/53* (2013.01)

(58) Field of Classification Search
CPC .................................................. A61K 31/506
See application file for complete search history.

(56) References Cited

U.S. PATENT DOCUMENTS

| | | | |
|---|---|---|---|
| 4,085,225 A | 4/1978 | Welle et al. | |
| 4,136,193 A | 1/1979 | Bogeso et al. | |
| 6,838,465 B2 | 1/2005 | Yamada et al. | |
| 7,279,578 B2 | 10/2007 | Aissaoui et al. | |
| 7,396,958 B2 | 7/2008 | Courtemanche et al. | |
| 7,435,815 B2 | 10/2008 | Aissaoui et al. | |
| 7,538,109 B2 | 5/2009 | Aissaoui et al. | |
| 7,553,836 B2 | 6/2009 | Zhao | |
| 7,763,638 B2 | 7/2010 | Aissaoui et al. | |
| 7,812,031 B2 | 10/2010 | Aranyi et al. | |
| 7,834,028 B2 | 11/2010 | Aissaoui et al. | |
| 7,851,622 B2 | 12/2010 | Washburn et al. | |
| 7,923,470 B2 | 4/2011 | Knust et al. | |
| 7,932,246 B2 | 4/2011 | Moffat et al. | |
| 7,951,797 B2 | 5/2011 | Breslin et al. | |
| 7,956,049 B2 | 6/2011 | Zhao | |
| 7,968,534 B2 | 6/2011 | Despeyroux et al. | |
| 7,973,159 B2 | 7/2011 | Washburn et al. | |
| 7,994,336 B2 | 8/2011 | Aissaoui et al. | |
| 8,012,984 B2 | 9/2011 | Stein et al. | |
| 8,067,420 B2 | 11/2011 | Stein et al. | |

(Continued)

FOREIGN PATENT DOCUMENTS

| | | |
|---|---|---|
| AU | 2010310595 B2 | 7/2015 |
| EP | 1288202 A1 | 3/2003 |

(Continued)

OTHER PUBLICATIONS

Aissaoui et al., "N-Glycine-sulfonamides as potent dual orexin 1/orexin 2 receptor antagonists", Bioorganic & Medicinal Chemistry Letters, Nov. 2008, 18, 5729-5733.
Arendt et al., "Anxiolytic function of the orexin 2/hypocretin A receptor in the basolateral amygdala", Psychoneuroendocrinology, Feb. 2014, 40, 17-26.
Asnis et al., "Zolpidem for persistent insomnia in SSRI-treated depressed patients", J. Clin. Psychiatry, Oct. 1999, 60(10), 668-676.
Aston-Jones, G. et al., "Role of lateral hypothalamic orexin neurons in reward processing and addiction" Neuropharmacology 2009, 56 Supp.I 1:pp. 112-121.
Bagshawe, K., "Antibody-Directed Enzyme Prodrug Therapy: A Review" Drug Development Research 34:220-230, 1995.

(Continued)

*Primary Examiner* — Kevin E Weddington
(74) *Attorney, Agent, or Firm* — BakerHostetler

(57) ABSTRACT

The present disclosure is directed to, inter alia, methods of treating a subject suffering from or diagnosed with depression, comprising administering to a subject in need of such treatment an effective amount of a compound of formula (I), or a pharmaceutically acceptable salt thereof, wherein $R^1$ to $R^4$ are described herein and wherein the compound is administered prior to sleep.

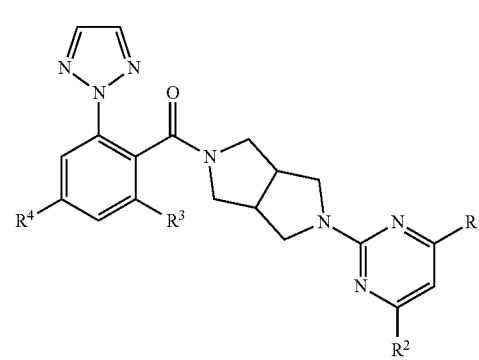

(I)

30 Claims, 9 Drawing Sheets

(56) References Cited

U.S. PATENT DOCUMENTS

| | | |
|---|---|---|
| 8,093,255 B2 | 1/2012 | Alvaro et al. |
| 8,106,215 B2 | 1/2012 | Aissaoui et al. |
| 8,129,384 B2 | 3/2012 | Alvaro et al. |
| 8,133,908 B2 | 3/2012 | Alvaro et al. |
| 8,188,082 B2 | 5/2012 | Aissaoui et al. |
| 8,207,220 B2 | 6/2012 | Knust et al. |
| 8,236,964 B2 | 8/2012 | Aissaoui et al. |
| 8,288,411 B2 | 10/2012 | Aissaoui et al. |
| 8,288,429 B2 | 10/2012 | Aissaoui et al. |
| 8,357,700 B2 | 1/2013 | Cox et al. |
| 8,362,009 B2 | 1/2013 | Bergman et al. |
| 8,563,539 B2 | 10/2013 | Baldino et al. |
| 8,598,119 B2 | 12/2013 | Mates et al. |
| 8,623,863 B2 | 1/2014 | Coleman et al. |
| 8,653,263 B2 | 2/2014 | Chai et al. |
| 8,680,275 B2 | 3/2014 | Branstetter et al. |
| 8,748,430 B2 | 6/2014 | Knust et al. |
| 8,877,773 B2 | 11/2014 | Shekhar et al. |
| 9,029,364 B2 | 5/2015 | Kuduk et al. |
| 9,079,911 B2 | 7/2015 | Chai et al. |
| 9,157,077 B2 | 10/2015 | Baldino et al. |
| 9,168,258 B2 | 10/2015 | Mates et al. |
| 9,266,870 B2 | 2/2016 | Futamura et al. |
| 9,586,934 B2 | 3/2017 | Kuduk et al. |
| 9,586,962 B2 | 3/2017 | Letavic et al. |
| 9,624,197 B2 | 4/2017 | Kuduk et al. |
| 9,695,163 B2 | 7/2017 | Liverton et al. |
| 9,845,333 B2 | 12/2017 | Gelin et al. |
| 10,196,383 B2 | 2/2019 | Zhang et al. |
| 10,611,760 B2 | 4/2020 | Blaney et al. |
| 10,696,654 B2 | 6/2020 | Martin |
| 10,828,302 B2 * | 11/2020 | De Boer ............... A61K 47/38 |
| 2002/0019388 A1 | 2/2002 | Schrimpf et al. |
| 2004/0242641 A1 | 12/2004 | Buckley et al. |
| 2005/0065178 A1 | 3/2005 | Basha et al. |
| 2005/0101602 A1 | 5/2005 | Basha et al. |
| 2005/0176680 A1 | 8/2005 | Lalji et al. |
| 2006/0019985 A1 | 1/2006 | Ma et al. |
| 2006/0074121 A1 | 4/2006 | Chen et al. |
| 2006/0178515 A1 | 8/2006 | Aissaoui et al. |
| 2006/0241102 A1 | 10/2006 | Kase et al. |
| 2006/0258672 A1 | 11/2006 | Barbosa et al. |
| 2006/0258691 A1 | 11/2006 | Barbosa et al. |
| 2008/0009477 A1 | 1/2008 | Hutchison et al. |
| 2008/0132490 A1 | 6/2008 | Bergman et al. |
| 2008/0153811 A1 | 6/2008 | Barbosa et al. |
| 2008/0175795 A1 | 7/2008 | Neogi et al. |
| 2009/0011994 A1 | 1/2009 | Stein et al. |
| 2009/0022670 A1 | 1/2009 | Alvaro et al. |
| 2009/0036422 A1 | 2/2009 | Knust et al. |
| 2009/0054439 A1 | 2/2009 | Courtemanche et al. |
| 2009/0163485 A1 | 6/2009 | Knust et al. |
| 2009/0176789 A1 | 7/2009 | Breslin et al. |
| 2009/0306100 A1 | 12/2009 | Barbosa et al. |
| 2010/0016401 A1 | 1/2010 | Aissaoui et al. |
| 2010/0029617 A1 | 2/2010 | Aissaoui et al. |
| 2010/0105614 A1 | 4/2010 | Jochelson |
| 2010/0144760 A1 | 6/2010 | Alvaro et al. |
| 2010/0160344 A1 | 6/2010 | Alvaro et al. |
| 2010/0160345 A1 | 6/2010 | Alvaro et al. |
| 2010/0168131 A1 | 7/2010 | Alvaro et al. |
| 2010/0184808 A1 | 7/2010 | Aissaoui et al. |
| 2010/0197733 A1 | 8/2010 | Aissaoui et al. |
| 2010/0210667 A1 | 8/2010 | Alvaro et al. |
| 2010/0256121 A1 | 10/2010 | Bergman et al. |
| 2010/0256182 A1 | 10/2010 | Aissaoui et al. |
| 2010/0267730 A1 | 10/2010 | Alvaro et al. |
| 2011/0009461 A1 | 1/2011 | Aissaoui et al. |
| 2011/0053979 A1 | 3/2011 | Alvaro et al. |
| 2011/0077200 A1 | 3/2011 | Jochelson et al. |
| 2011/0152235 A1 | 6/2011 | Baldino et al. |
| 2011/0207715 A1 | 8/2011 | Cox et al. |
| 2011/0257198 A1 | 10/2011 | Alvaro et al. |
| 2011/0263643 A1 | 10/2011 | Cox et al. |
| 2011/0288098 A1 | 11/2011 | Alvaro et al. |
| 2012/0040991 A1 | 2/2012 | Amantini et al. |
| 2012/0095034 A1 | 4/2012 | Alvaro et al. |
| 2012/0149711 A1 | 6/2012 | Di Fabio |
| 2012/0149723 A1 | 6/2012 | Di Fabio |
| 2012/0202783 A1 | 8/2012 | Branstetter et al. |
| 2012/0208812 A1 | 8/2012 | Chai et al. |
| 2013/0005655 A1 | 1/2013 | Jochelson et al. |
| 2013/0210911 A1 | 8/2013 | Lee et al. |
| 2013/0281465 A1 | 10/2013 | Nozawa et al. |
| 2014/0081025 A1 | 3/2014 | Suzuki et al. |
| 2014/0107084 A1 | 4/2014 | Jochelson et al. |
| 2014/0171430 A1 | 6/2014 | Letavic et al. |
| 2014/0179697 A1 | 6/2014 | Chai et al. |
| 2014/0228377 A1 | 8/2014 | Abe et al. |
| 2014/0275050 A1 | 9/2014 | Kuduk et al. |
| 2014/0364432 A1 | 12/2014 | Kamenecka et al. |
| 2014/0364433 A1 | 12/2014 | Kamenecka et al. |
| 2015/0011613 A1 | 1/2015 | Shekhar et al. |
| 2015/0018309 A1 | 1/2015 | Lindsley et al. |
| 2015/0166523 A1 | 6/2015 | Araki et al. |
| 2015/0183768 A1 | 7/2015 | Futamura et al. |
| 2015/0322039 A1 | 11/2015 | Kuduk et al. |
| 2015/0335651 A1 | 11/2015 | Chai et al. |
| 2016/0030425 A1 | 2/2016 | Mates et al. |
| 2016/0051533 A1 | 2/2016 | Ladd |
| 2016/0185768 A1 | 6/2016 | Liverton et al. |
| 2016/0368898 A1 | 12/2016 | Kuduk et al. |
| 2017/0015651 A1 | 1/2017 | Gelin et al. |
| 2017/0129901 A1 | 5/2017 | Chai et al. |
| 2018/0282309 A1 | 10/2018 | Fieldhouse et al. |

FOREIGN PATENT DOCUMENTS

| | | |
|---|---|---|
| EP | 2295437 A1 | 3/2011 |
| EP | 2653469 A1 | 10/2013 |
| EP | 2708537 A1 | 3/2014 |
| EP | 2730573 A1 | 5/2014 |
| EP | 2862855 A1 | 4/2015 |
| EP | 2862860 A1 | 4/2015 |
| EP | 2491038 B1 | 4/2016 |
| JP | 2003-531210 A | 10/2003 |
| JP | 2009-506061 A | 2/2009 |
| JP | 2014-015452 A | 1/2014 |
| JP | 2014-111586 A | 6/2014 |
| JP | 2014-141480 A | 8/2014 |
| JP | 2015-131802 A | 7/2015 |
| JP | 2015-131803 A | 7/2015 |
| JP | 2016-028017 A | 2/2016 |
| WO | 96/39407 | 12/1996 |
| WO | 97/11945 | 4/1997 |
| WO | 00/55143 | 9/2000 |
| WO | 01/61347 A1 | 8/2001 |
| WO | 01/81347 A2 | 11/2001 |
| WO | 01/85693 A1 | 11/2001 |
| WO | 02/60902 | 8/2002 |
| WO | 02/70523 | 9/2002 |
| WO | 02/70527 | 9/2002 |
| WO | 03/02561 | 1/2003 |
| WO | 03/02581 | 1/2003 |
| WO | 03/51672 | 6/2003 |
| WO | 03/51872 | 6/2003 |
| WO | 2003/106450 | 12/2003 |
| WO | 2004/004733 A1 | 1/2004 |
| WO | 2004/033418 A2 | 4/2004 |
| WO | 2004/041791 A1 | 5/2004 |
| WO | 2004/085403 A1 | 10/2004 |
| WO | 2004/096780 A1 | 11/2004 |
| WO | 2005/005439 A1 | 1/2005 |
| WO | 2005/023231 A1 | 3/2005 |
| WO | 2005/084667 A1 | 9/2005 |
| WO | 2005/118548 A1 | 12/2005 |
| WO | 2006/012396 A1 | 2/2006 |
| WO | 2006/024779 A1 | 3/2006 |
| WO | 2006/052542 A2 | 5/2006 |
| WO | 2006/056848 A1 | 6/2006 |
| WO | 2006/067121 A1 | 6/2006 |
| WO | 2006/123121 A1 | 11/2006 |
| WO | 2006/124748 A2 | 11/2006 |
| WO | 2006/124897 A2 | 11/2006 |

(56) References Cited

FOREIGN PATENT DOCUMENTS

| | | |
|---|---|---|
| WO | 2007/007069 A1 | 1/2007 |
| WO | 2007/025069 A2 | 3/2007 |
| WO | 2007/085718 A1 | 8/2007 |
| WO | 2007/088276 A2 | 8/2007 |
| WO | 2007/092416 A2 | 8/2007 |
| WO | 2007/122591 A2 | 11/2007 |
| WO | 2007/126934 A2 | 11/2007 |
| WO | 2007/126935 A2 | 11/2007 |
| WO | 2007/146761 A2 | 12/2007 |
| WO | 2008/008517 A2 | 1/2008 |
| WO | 2008/008518 A1 | 1/2008 |
| WO | 2008/008551 A2 | 1/2008 |
| WO | 2008/020405 A2 | 2/2008 |
| WO | 2008/026149 A1 | 3/2008 |
| WO | 2008/034731 A1 | 3/2008 |
| WO | 2008/038251 A2 | 4/2008 |
| WO | 2008/052139 A2 | 5/2008 |
| WO | 2008/067121 A2 | 6/2008 |
| WO | 2008/069997 A1 | 6/2008 |
| WO | 2008/078291 A1 | 7/2008 |
| WO | 2008/117241 A2 | 10/2008 |
| WO | 2008/134480 A1 | 11/2008 |
| WO | 2008/143856 A1 | 11/2008 |
| WO | 2009/003993 A1 | 1/2009 |
| WO | 2009/003997 A1 | 1/2009 |
| WO | 2009/004584 A1 | 1/2009 |
| WO | 2009/009501 A2 | 1/2009 |
| WO | 2009/011775 A1 | 1/2009 |
| WO | 2009/016087 A1 | 2/2009 |
| WO | 2009/016286 A2 | 2/2009 |
| WO | 2009/016564 A2 | 2/2009 |
| WO | 2009/022311 A2 | 2/2009 |
| WO | 2009/037394 A2 | 3/2009 |
| WO | 2009/040730 A2 | 4/2009 |
| WO | 2009/058238 A1 | 5/2009 |
| WO | 2009/061197 A1 | 5/2009 |
| WO | 2009/081197 A1 | 7/2009 |
| WO | 2009/124956 A1 | 10/2009 |
| WO | 2009/145900 A1 | 12/2009 |
| WO | 2010/012620 A1 | 2/2010 |
| WO | 2010/017260 A1 | 2/2010 |
| WO | 2010/048010 A1 | 4/2010 |
| WO | 2010/048012 A1 | 4/2010 |
| WO | 2010/048013 A1 | 4/2010 |
| WO | 2010/048014 A1 | 4/2010 |
| WO | 2010/048016 A1 | 4/2010 |
| WO | 2010/048017 A1 | 4/2010 |
| WO | 2010/051236 A1 | 5/2010 |
| WO | 2010/051237 A1 | 5/2010 |
| WO | 2010/051238 A1 | 5/2010 |
| WO | 2010/060470 A1 | 6/2010 |
| WO | 2010/060471 A1 | 6/2010 |
| WO | 2010/060472 A1 | 6/2010 |
| WO | 2010/063662 A1 | 6/2010 |
| WO | 2010/063663 A1 | 6/2010 |
| WO | 2010/072722 A1 | 7/2010 |
| WO | 2010/098911 A2 | 9/2010 |
| WO | 2010/122151 A1 | 10/2010 |
| WO | 2011/023578 A1 | 3/2011 |
| WO | 2011/023585 A1 | 3/2011 |
| WO | 2011/050198 A1 | 4/2011 |
| WO | 2011/050200 A1 | 4/2011 |
| WO | 2011/050202 A1 | 4/2011 |
| WO | 2011/057471 A1 | 5/2011 |
| WO | 2012/081692 A1 | 6/2012 |
| WO | 2012/089606 A1 | 7/2012 |
| WO | 2012/089607 A1 | 7/2012 |
| WO | 2012/145581 A1 | 10/2012 |
| WO | 2012/153729 A1 | 11/2012 |
| WO | 2013/005755 A1 | 1/2013 |
| WO | 2013/059163 A1 | 4/2013 |
| WO | 2013/119639 A1 | 8/2013 |
| WO | 2013/187466 A1 | 12/2013 |
| WO | 2013/187467 A1 | 12/2013 |
| WO | 2014/085208 A1 | 6/2014 |
| WO | 2014/091876 A1 | 6/2014 |
| WO | 2015/020933 A1 | 2/2015 |
| WO | 2015/085004 A1 | 6/2015 |
| WO | 2015/088865 A1 | 6/2015 |
| WO | 2015/095108 A1 | 6/2015 |
| WO | 2015/123355 A1 | 8/2015 |
| WO | 2015/152367 A1 | 10/2015 |
| WO | 2015/152368 A1 | 10/2015 |
| WO | 2015/180060 A1 | 12/2015 |
| WO | 2016/025669 A1 | 2/2016 |
| WO | 2020/120994 A1 | 6/2020 |

OTHER PUBLICATIONS

Baxter et al., "The First Large-Scale Synthesis of MK-4305: A Dual Orexin Receptor Antagonist for the Treatment of Sleep Disorder", Organic Process Research & Development, Mar. 2011, 15, 367-375.
Berg, S. et al., "Pharmaceutical Salts" Journ. of Pharm. Sciences, 1977, 66:1-19, & Handbook of Pharmaceutical Salts, Properties, Selection & Use, Stahl and Wermuth, Eds., Wiley-VCH and VHCA, Zurich.
Bergman et al., "Proline bis-amides as potent dual orexin receptor antagonists", Bioorganic & Medicinal Chemistry Letters, Feb. 2008, 18, 1425-1430.
Bertolini, G., et al., "A New Rational Hypothesis for the Pharmacophore of the Active Metabolite of Leflunomide, a Potent Immunosuppressive Drug", J. Med. Chem 1997, 40, 2011-2016.
Betschart et al., "Identification of a Novel Series of Orexin Receptor Antagonists with a Distinct Effect on Sleep Architecture for the Treatment of Insomnia", Journal of Medicinal Chemistry, Oct. 2013, 56, 7590-7607.
Bettica et al., "Phase I studies on the safety, tolerability, pharmacokinetics and pharmacodynamics of SB-649868, a novel dual orexin receptor antagonist", Journal of Psychopharmacology, Aug. 2012, 26(8), 1058-1070.
Bettica et al., "The Orexin Antagonist Sb-649868 Promotes and Maintains Sleep in Men with Primary Insomnia", Sleep, Aug. 2012, 35(8), 1097-1104.
Bodor, N., "Novel Approaches to the Design of Safer Drugs: Soft Drugs and Site-Specific Chemical Delivery Systems", Advanced Drug Res., 1984 13, 224-231.
Boss et al. "Biomedical Application of Orexin/Hypocretin Receptor Ligands in Neuroscience", J. Med. Chem., 2009, 52(4), pp. 891-903.
Brisbare-Roch et al., "Promotion of sleep by targeting the orexin system in rats, dogs and humans", Nature Medicine, Feb. 2007, 13(2), 150-155.
Brosschot et al., "The perseverative cognition hypothesis: a review of worry, prolonged stress-related physiological activation, and health", J. Psychosomatic Res., Feb. 2006, 60, 113-124.
Brosschot, "Markers of chronic stress: prolonged physiological activation and (un)conscious perseverative cognition", neuroscience and Behavioral Rev., Sep. 2010, 35, 46-50.
Bundgaard, H. (Ed.), "Design of Prodrugs", Elsevier, 1985, 4 pages.
Chang et al., "Inhibitory effects of an orexin-2 receptor antagonist on orexin A-and stress-induced ACTH responses in conscious rats", Neuroscience Res., Mar. 2007, 57, 462-466.
Chemelli et al., "Narcolepsy in orexin knockout mice: Molecular genetics of sleep regulation", Cell, Aug. 1999, 98, 437-451.
Chen et al. "Pressor effects of orexins injected intracistemally and to rostral ventrolateral medulla of anesthetized rats", Am. J. Physiol., 2000, 278, pp. R692-R697.
Chen et al., "The Hypocretin/orexin system: An increasingly important role in neuropsychiatry", Medicinal Research reviews, Jan. 2015, 35(1), 152-197.
Chilean Application No. 1162-2010: Exam Report dated May 9, 2012, 6 pages.
Christopher, "Small-molecule antagonists of the orexin receptors", Pharmaceutical Patent Analyst, Pharm. Pat. Anal., Nov. 2014, 3(6), 625-638.
Clinical Trial NCT02476058 Report, ClinicalTrials.gov, dated Mar. 7, 2016.

(56) References Cited

OTHER PUBLICATIONS

Clinical Trial NCT02067299 Report, ClinicalTrials.gov, dated Feb. 3, 2016.
Clinical Trial NCT02230878 Report, ClinicalTrials.gov, dated Jan. 27, 2016.
Clinical Trial NCT02455856 Report, ClinicalTrials.gov, dated Jul. 24, 2015.
Clinical Trial NCT02464046 Report, ClinicalTrials.gov, dated Feb. 18, 2016.
Clinical Trial NCT02555124 Report, ClinicalTrials.gov, dated Feb. 22, 2016.
Clinical Trial NCT02578472 Report, ClinicalTrials.gov, dated Feb. 4, 2016.
Clinical Trial NCT02617810 Report, ClinicalTrials.gov, dated Feb. 19, 2016.
Clinical Trial NCT02661893 Report, ClinicalTrials.gov, dated Feb. 18, 2016.
Clinical Trial NCT03227224 Report, ClinicalTrials.gov, dated Jul. 21, 2017.
Clinical Trial NCT03375203 Report, ClinicalTrials.gov, dated Dec. 14, 2017.
Clinical Trial NCTNCT03321526 Report, ClinicalTrials.gov, dated Oct. 23, 2017.
Coleman et al "Discovery of 3,9-diazabicyclo[4.2.1]nonanes as potent dual orexin receptor antagonists with sleep-promoting activity in the rat" Bioorganic & Medicinal Chemistry Letters, 2010, 20 pp. 4201-4205.
Coleman et al. "Design and synthesis of conformationally constrained N, N-disubstituted 1,4-diazepanes as potent orexin receptor antagonists" Bioorganic & Medicinal Chemistry Letters, 2010, 20 pp. 2311-2315.
Coleman et al., "Discovery of [(2R,5R)-5-{[(5-Fluoropyridin-2-yl)oxy]methyl}-2-methylpiperidin-1-yl][5-methyl-2-(pyrimidin-2-yl)phenyl]methanone (MK-6096): A Dual Orexin Receptor Antagonist with Potent Sleep-Promoting Properties", Chem Med Chem, Mar. 2012, 7, 415-424.
Considine, G.D., ed., Van Nostrand's Encyclopedia of Chemistry, 5th ed. 2005 p. 261.
Covington et al., Handbook of Chemistry and Physics, 84th ed., 2003-2004 pp. 8-37 to 8-44.
Cox et al., "Conformational analysis of N,N-disubstituted-1,4-diazepane orexin receptor antagonists and implications for receptor binding", Bioorganic & Medicinal Chemistry Letters, Jun. 2009, 19, 2997-3001.
Cox et al., "Discovery of the dual orexin receptor antagonist [(7R)-4-(5-chloro-1,3-benzoxazol-2-yl)-7-methyl-1,4-diazepan-1-yl][(5-methyl-2-(2H-1,2,3-triazol-2-yl)phenyl] nethanone (MK-4305) for the treatment of insomnia" Journal of Medicinal Chemistry 2010, 53(14):pp. 5320-5332.
Cruz et al., "Interaction study between almorexant, a dual orexin receptor antagonist, and desipramine in healthy male subjects", European Neuropsychopharmacology, Aug. 2010, Vo. 20, Suppl. 3, S253, Abstract No. P.1.c.032.
Dayas, C. V. et al., "Stimuli linked to ethanol availability activate hypothalamic CART and orexin neurons in a reinstatement model of relapse", Biological Psychiatry, Jan. 2008, 63(2),152-157.
De Lecea et al., "Optogenetic control of hypocretin/orexin neurons", Abstracts of Papers, 248th ACS National Meeting & Exposition, Aug. 2014, 1 page.
De Lecea et al., "The hypocretins: Hypothalamus-specific peptides with neuroexcitatory activity", Proc. Natl. Acad. Sci., Jan. 1998, 95, 322-327.
Difabio et al., "Discovery process and pharmacological characterization of a novel dual orexin 1 and orexin 2 receptor antagonist useful for treatment of sleep disorders", Bioorganic & Medicinal Chemistry Letters, Sep. 2011, 21, 5562-5567.
Dugovic et al., "Blockade of Orexin-1 Receptors Attenuates Orexin-2 Receptor Antagonism-Induced Sleep Promotion in the Rat", The Journal of Pharmacology and Experimental Therapeutics, Jul. 2009, 330(1), 142-151.
Dugovic et al., "Orexin-1 receptor blockade dysregulates REM sleep in the presence of orexin-2 receptor antagonism" Frontiers in Neuroscience, Feb. 2014, vol. 8, Article 29, 1-8.
European Patent Application. No. 10773477.4: Communication pursuant to Article 94(3) EPC dated Apr. 19, 2013, 3 pages.
Feng et al., "Brain orexins and wake regulation in rats exposed to maternal deprivation", Brain Research, Jun. 2007, 1154, 163-172.
Fitch et al., "LSN2424100: a novel, potent orexin-2 receptor antagonist with selectivity over orexin-1 receptors and activity in an animal model predictive of antidepressant-like efficacy", Frontiers in Neuroscience, Jan. 2014, 8, Article 5, 11 pages.
Fleisher, D. et al., "Improved Oral Drug Delivery: Solubility Limitations Overcome by the Use of Prodrugs", Advanced Drug Delivery Reviews, May 1996, 19, 115-130.
Frost, J., et al., "Synthesis and Structure-Activity Relationships of 3,8-Diazabicylclo [4.2.0] Octane Ligands, Potent Nicotinic Acetylcholine Receptor Agonists" J. Med. Chem. 2006, 49, 7843-7851.
Fujimoto et al., "Discovery of potent, selective, orally active benzoxazepine-based Orexin-2 receptor antagonists", Bioorganic & Medicinal Chemistry Letters, Nov. 2011, 21, 6414-6416.
Fujimoto et al., "Discovery of spiropiperidine-based potent and selective Orexin-2 receptor antagonists", Nov. 2011, 21, 6409-6413.
Gaffield et al., "Orexin Receptor Antagonists: A New Concept in CNS Disorders?", Chem Med Chem, Aug. 2010, 5, 1197-1214.
Georgescu, D. et al., "Involvement of the lateral hypothalamic peptide orexin in morphine dependence and withdrawal" Journal of Neuroscience 2003, 23(8), pp. 3106-3111.
Girardin et al., "Convergent Kilogram-Scale Synthesis of Dual Orexin Receptor Antagonist", Organic Process Research & Development, Jan. 2013, 17, 61-68.
Goldberg et al., "The importance of anxiety in both major depression and bipolar disorder", Depression and Anxiety, Jan. 2012, 29, 471-478.
Goiter et al., "International Union of Basic and Clinical Pharmacology. LXXXVI. Orexin Receptor Function, Nomenclature and Pharmacology", Pharmacological Reviews, Jul. 2012, 64(3), 389-420.
Gotter et al., "Orexin receptors as therapeutic drug targets", Progress in Brain Research, 2012, 198, 163-188.
Gozzi et al., "Functional Magnetic Resonance Imaging Reveals Different Neural Substrates for the Effects of Orexin-1 and Orexin-2 Receptor Antagonists", PLoS One, Jan. 2011, 6(1), e16406, 12 pages.
Gulbahar et al., "P-169, Plasma Orexin-A Levels of Patients With Major Depression", Turkish Journal of Biochemistry, 22th National Biochemistry Congress, Oct. 27-30, 2010, vol. 35, Issue 1, 2 pages.
Hamlin, A. S. et al., "The neural correlates and role of D1 dopamine receptors in renewal of extinguished alcohol-seeking" Neuroscience 2007, 146(2) pp. 525-536.
Hara et al. "Genetic ablation of orexin neurons in mice results in narcolepsy, hypophagia, and obesity", Neuron, 2001, 30 (2), pp. 345-354.
Hassani et al., "Orexin Neurons Respond Differentially to Auditory Cues Associated with Appetitive versus Aversive Outcomes", J. Neuroscience, Feb. 2016, 36(5), 1747-1757.
Hirose et al., "N-Acyl 6,7-Dimethoxy-1,2,3,4-tetrahydroisoquinoline: The First Orexin-2 Receptor Selective Non-peptidic Antagonist", Bioorganic & Medicinal Chemistry Letters, Dec. 2003, 13, 4497-4499.
International Patent Application No. PCT/US2010/053606: International Search Report dated Jan. 12, 2011, 3 pages.
International Patent Application No. PCT/US2010/053609: International Search Report dated Jan. 24, 2011, 3 pages.
International Patent Application No. PCT/US2010/053611: International Search Report dated Dec. 10, 2010, 4 pages.
International Search Report and Written Opinion dated Jun. 6, 2017 issued in International Patent Application No. PCT/US17/21565.
Jiang et al., "Disubstituted piperidines as potent orexin (hypocretin) receptor antagonists", Bioorganic & Medicinal Chemistry Letters, Jun. 2012, 22, 3890-3894.
Johnson et al., "A key role for orexin in panic anxiety", Nature Medicine, Jan. 2010, vol. 16, No. 1, 111-115.

(56) References Cited

OTHER PUBLICATIONS

Johnson et al., "Orexin, stress, and anxiety/panic states", Progress in Brain Research, 2012, 198, 133-161.
Kane, J.K. et al., "Hypothalamic orexin-A binding sites are downregulated by chronic nicotine treatment in the rat" Neuroscience Letters 2001, 298(1):pp. 1-4.
Kane, J.K. et al., "Nicotine Up-Regulates Expression of Orexin and Its Receptors in Rat Brain" Endocrinology 2000 141(10). pp. 3623-3629.
Kang et al., "Amyloid-.beta. Dynamics Are Regulated by Orexin and the Sleep-Wake Cycle", Science Express, 2009, pp. 1-10.
Kirchgessner and Liu "Orexin synthesis and response in the gut", Neuron, 1999, 24 (4), pp. 941-951.
Kuduk et al., "Orexin receptor antagonists in development for Insomnia and CNS disorders", Annual Reports in medicinal Chemistry, 2013, 48, 73-87.
Kuduk et al., "Synthesis and evaluation of carbon-linked analogs of dual orexin receptor antagonist filorexant", Bioorganic & Medicinal Chemistry Letters, Apr. 2014, 24, 1784-1789.
Kuehn et al., "Hormone may play role in triggering panic attacks", Journal of the American Medical Association, Feb. 10, 2010, 303, 6, 498.
Langmead et al. "Characterisation of the binding of (3H)-SB-674042, a novel nonpeptide antagonist, to the human orexin 1 receptor", British Journal of Pharmacology 2004, 141 (2), pp. 340-346.
Larsen, Design and Application of Prodrugs, Drug Design and Development 1991 (Krogsgaard-Larsen, et al., eds., Harwood Academic Publishers.
Lawrence, et al., "The orexin system regulates alcohol-seeking in rats" British Journal of Pharmacology 2006, 148(6) pp. 752-759.
Lebold et al., "Selective orexin receptor antagonists", Bioorganic & Medicinal Chemistry Letters, Sep. 2013, 23, 4761-4769.
Lee, "Discharge of Identified Orexin/Hypocretin Neurons across the Sleep-Walking Cycle", J. Neuroscience, Jul. 2005, 25(8), 6716-6720.
Leman et al., "Role of orexin in the unpredictable chronic mild stress model of depression in mice", European Neuropsychopharmacology, Oct. 2012, 22, S2, S146, Abstract S.27.04.
Letavic et al., "Novel Octahydropyrrolo [3,4- c ]pyrroles Are Selective Orexin-2 Antagonists: SAR Leading to Clinical Candidate", Journal of Medicinal Chemistry, Jul. 8, 2015, vol. 58, No. 14, pp. 5620-5636.
Li et al., "Hypocretins, Neural Systems, Physiology, and Psychiatric Disorders", Current Psychiatry Reports, Jan. 1, 2016, 18, 1, 1-12.
Lin et al. "The sleep disorder canine narcolepsy is caused by a mutation in the hypocretin (orexin) receptor 2 gene", Cell 1999, 98, pp. 365-376.
Lovenberg et al., "Selective Orexin-2 Receptor Antagonism as Adjunctive Therapy for Insomnia in Depression", Neuropsychopharmacology, Dec. 2013, 38, S2, S543-S544.
Malherbe et al. "Biochemical and electrophysiological characterization of almorexant, a dual orexin 1 receptor (OX1)/orexin 2 receptor (OX2) antagonist comparison with selective OX1 and OX2 antagonists", Molecular Pharmacology 2009, 76(3) pp. 618-631.
Malherbe, P. et al., Biochemical and behavioural characterization of EMPA, a novel high-affinity, selective antagonist for the OX.sub.2 Receptor, British Journal of Pharmacology 2009 156:1326-1341.
Mang et al., "The Dual Orexin Receptor Antagonist Almorexant Induces Sleep and Decreases Orexin-Induced Locomotion by Blocking Orexin 2 Receptors", Sleep, Dec. 2012, 35(12), 1625-1635.
Manka, et al., "Octahydropyrrolo [3, 4-c]pyrrole negative allosteric modulators of mGlu1", Bioorganic & Medicinal Chemistry Letters, Pergamon, Amsterdam, NL, Jul. 23, 2013, vol. 23, No. 18, pp. 5091-5096.
Marcus et al., "Differential Expression of Orexin Receptors 1 and 2 in the Rat Brain", Journal of Comparative Neurology, Jun. 2001, 435, 6-25.

McAtee et al., "Novel substituted 4-phenyl-[1,3]dioxanes: potent and selective orexin receptor 2 (OX2R) antagonists", Bioorganic & Medicinal Chemistry Letters, Aug. 2004, 14, 4225-4229.
McElhinny Jr. et al., "Hydrolytic instability of the important orexin 1 receptor antagonist SB-334867: Possible confounding effects on in vivo and in vitro studies", Bioorganic & Medicinal Chemistry Letters, Nov. 2012, 22, 6661-6664.
Minerva Press Release, Jan. 21, 2015.
Minerva Press Release, Jun. 16, 2015.
Minerva Press Release, Mar. 11, 2016.
Minerva Press Release, Sep. 22, 2014.
Minerva Press Release, Sep. 24, 2015.
Moffitt et al., "Depression and generalized anxiety disorder. Cumulative and sequential comorbidity in a birth cohort followed prospectively to age 32 years", Arch Gen. Psychiatry, Jun. 2007, 64, 651-660.
Nakamura at al. "Orexin-induced hyperlocomotion end stereotypy are mediated by the dopaminergic system", Brain Res. 2000, 873 (1) pp. 181-187.
Nambu et al., "Distribution of orexin neurons in the adult rat brain", Brain Research, May 1999, 827, 243-260.
Nollet et al., "Activation of orexin neurons in dorsomedial/ perifornical hypothalamus and antidepressant reversal in a rodent model of depression", Neuropharmacology, Jul.-Aug. 2011, 61(1-2), 336-346.
Nollet et al., "Neurogenesis-Independent Antidepressant-Like Effects on Behavior and Stress Axis Response of a Dual Orexin Receptor Antagonists in a Rodent Model of Depression", Neuropsychopharmacology, Sep. 2012, 37, 2210-2221.
Nollet et al., "Role of Orexin in the Pathophysiology of Depression: Potential for Pharmacological Intervention", CNS Drugs, Jun. 2013, 27(6), 411-422.
Oi et al., "Synthesis and Evaluation of Novel Radioligands for Positron Emission Tomography Imaging of the Orexin-2 Receptor", Journal of Medicinal Chemistry, Jul. 2013, 56, 6371-6385.
P. Bonaventure et al., Characterization of JNJ-42847922, a Selective Orexin-2 Receptor Antagonist, as a Clinical Candidate for the Treatment of Insomnia. J. Pharmacol. Exp. Ther., Aug. 4, 2015, vol. 354, No. 3, pp. 471-482.
Panksepp et al., "Dynorphin and orexin interactions in the development and expression of depression-related anhedonia", Neuropsychopharmacology, Dec. 2011, 36, S1, S432-S433, Abstract 196.
Paulekuhn, "Trends in Active Pharmaceutical Ingredient Salt Selection based on Analysis of the Orange Book Database", J. Med. Chem., Dec. 2007, 50, 6665-6672.
Perrey et al., "Diaryl urea analogues of SB-334867 as orexin-1 receptor antagonists", Bioorganic & Medicinal Chemistry Letters, May 2011, 21, 2980-2985.
Perrey et al., "Substituted Tetrahydroisoquinolines as Selective Antagonists for the Orexin 1 Receptor", Journal of Medicinal Chemistry, Sep. 2013, 56, 6901-6916.
Peyron et al. "A mutation in a case of early onset narcolepsy and a generalized absence of hypocretin peptides in human narcoleptic brains", Nature Med. 2000, 6 (9), pp. 991-997.
Peyron et al. "Neurons containing hypocretin (Orexin) project to multiple neuronal systems" J. Neurosci., 1998, 18(23), pp. 9996-10015.
Piper et al. "The novel brain neuropeptide, orexin-A, modulates the sleep-wake cycle of rats", European Journal of Neuroscience, 2000, 12 (2), pp. 726-730.
Porter et al., "1,3-Biarylureas as Selective Non-peptide Antagonists of the Orexin-1 Receptor", Bioorganic & Medicinal Chemistry Letters, Jul. 2001, 11, 1907-1910.
Poupaert, "Drug Design: Basic Principles and Applications", Encyclopedia of Pharmaceutical Technology, 2007, 1362-1369.
Renzulli et al., "Disposition and Metabolism of [.sup.14C]SB-649868, an Orexin 1 and 2 Receptor Antagonist, in Humans", Drug Metabolism and Disposition, Feb. 2011, 39(2), 215-227.
Renzulli et al., "Disposition and Metabolism of [14C]SB-649868, an Orexin 1 and 2 Receptor Antagonist, in Humans", Drug Metabolism and Disposition, Feb. 2011, 39(2), 215-227.

(56) References Cited

OTHER PUBLICATIONS

Richards, J.K. et al., "Inhibition of orexin-1/hypocretin-1 receptors inhibits yohimbine-induced reinstatement of ethanol and sucrose seeking in Long-Evans rats" Psychophemacoloty 2008, 199(1):pp. 109-117.
Robinson, "Discovery of the Hemifumarate and (Alpha)-L-Alanyloxy)methyl Ether as Prodrugs of an Antirheumatic Oxindole: Prodrugs for the Enolic OH Group", J. Med. Chem., Jan. 1996, 39(1), 10-18.
Roecker et al., "Discovery of 5"-Chloro-N-[(5,6-dimethoxypyridin-2-yl)methyl]-2,2':5',3"- terpyridine-3'-carboxamide (MK-1064): A Selective Orexin 2 Receptor Antagonist (2-SORA) for the Treatment of Insomnia", Chem Med Chem, Feb. 2014, 9, 311-322.
Sakurai, T. "Orexins and orexin receptors: implication in feeding behavior" Regulatory Peptides 1999, 85(1): pp. 25-30.
Sakurai, T. et al., "Orexins and orexin receptors: a family of hypothalamic neuropeptides and G protein coupled receptors that regulate feeding behavior" Cell, Feb. 1998, 92(4), 573-585.
Sakurai, T., "The neural circuit of orexin (hypocretin): maintaining sleep and wakefulness", 2007, Nature Reviews Neuroscience, 8(3): pp. 171-181.
Samson et al. "Cardiovascular regulatory actions of the hypocretins in brain", Brain Res., 1999, 831: pp. 248-253.
Scammell et al., "Orexin Receptors: Pharmacology and Therapeutic Opportunities", Annual Review of Pharmacology and Toxicology, Feb. 2011, 51, 243-266.
Schneider, E. R., "Orexigenic peptides and alcohol intake: differential effects of orexin, gafanin, and ghrelin" Alcoholism: Clinical & Experimental Research 2007, 31(11):pp. 1858-1865.
Scott et al., "Hcrtr1 and 2 signaling differentially regulates depression-like behaviors", Behavioural Brain Research, Sep. 23, 2011, 222, 2, 289-294.
Shan, D. et al., "Prodrug Strategies Based on the Intramolecular Cyclization Reactions" J. Pharm. Sci., Jul. 1997, 86(7), 765-767.
Shirasaka et al."Sympathetic and cardiovascular actions of orexins in conscious rats", Am. J. Physio.., 1999, 277. pp. R1780-R1785.
Sifferlen et al., "Discovery of substituted lactams as novel dual orexin receptor antagonists. Synthesis, preliminary structure-activity relationship studies and efforts towards improved metabolic stability and pharmacokinetic properties. Part 1", Bioorganic & Medicinal Chemistry Letters, Feb. 24, 2014, 1201-1208.
Sifferlen et al., "Novel pyrazolo-tetrahydropyridines as potent orexin receptor antagonists", Bioorganic & Medicinal Chemistry Letters, Mar. 2010, 20, 1539-1542.
Sifferlen et al., "Structure-activity relationship studies and sleep-promoting activity of novel 1-chloro-5,6,7,8-tetrahydroimidazo[1,5-a Jpyrazine derivatives as dual orexin receptor antagonists. Part 2", Bioorganic & Medicinal Chemistry Letters, Jul. 2013, 23, 3857-3863.
Sifferlen et al., "Synthesis, structure-activity relationship studies, and identification of novel 5,6,7,8-tetrahydroimidazo[1,5-a ]pyrazine derivatives as dual orexin receptor antagonists. Part 1", Bioorganic & Medicinal Chemistry Letters, Apr. 2013, 23, 2212-2216.
Smart et al., "Orexins and the treatment of obesity", European Journal of Pharmacology, Apr. 2002, 440, 199-212.
Smart et al., "SB-334867-A: the first selective orexin-1 receptor antagonist", British Journal of Pharmacology, Mar. 2001, 132, 1179-1182.
Srinivasan et al., "Orexin Receptors Modulate Yohimbine-Induced Reinstatement of Ethanol Seeking and Gabaergic Transmission in the Central Amygdala", Alcoholism Clinical and Experimental Research, Jun. 2012, 36, S1, 116A.
Staner et al., "Comorbidity of insomnia and depression", Sleep Medicine Reviews, Feb. 2010, 14, 46-65.
Stasi et al., "Discovery, synthesis, selectivity modulation and Dmpk characterization of 5-azaspiro[2.4]heptanes as potent orexin receptor antagonists", Bioorganic & Medicinal Chemistry Letters, May 2013, 23, 2653-2658.
Steiner et al. "Discovery and Characterization of ACT-335827, an Orally Available, Brain Penetrant Orexin Receptor Type 1 Selective Antagonist", Chem Med Chem, Jun. 2013, 8, 898-903.
Steiner et al., "Opportunities and perspectives or developing orexin receptor antagonists", Frontiers in Science, Jun. 2014, vol. 8, Article 158, 1-2.
Steiner et al., "Opportunities and perspectivesfor developing orexin receptor antagonists", Frontiers in Science, Jun. 2014, vol. 8, Article 158, 1-2.
Steiner et al., "The brain orexin system and almorexant in fear-conditioned startle reactions in the rat", Psychopharmacology, Oct. 2012, 223, 465-475.
Sutcliffe et al., "The hypocretins: setting the arousal threshold", Nature Reviews Neuroscience, May 2002, 3, 339-349.
Takahashi et al. "Stimulation of gastric acid secretion by centrally administered orexin-A in conscious rats", Biochem. Biophys. Res. Commun., 1999, 254 (3), pp. 623-627.
Takahashi, "Neuronal activity of orexin and non-orexin waking-active neurons during wake-sleep states in the mouse", Neuroscience, May 2008, 153, 860-870.
Trivedi et al., "Distribution of orexin receptor mRNA in the rat brain", FEBS Letters, Sep. 1998, 438, 71-75.
Uno, "P.1.k.037 Prescription survey of orexin receptor antagonist suvorexant", European Neuropsychopharmacology, Sep. 2015, vol. 25, Supplement 2, S373-S374.
Ursin et al., "Cognitive activation theory of stress (CATS)", Neuroscience and Biobehavioral Rev, May 2010, 34, 877-881.
Ursin et al., "The cognitive activation theory of stress", Psychoneuroendocrinology, Jun. 2004, 29, 567-592.
Van Den Pohl, "Hypothalamic hypocretin (orexin): Robust innervation of the spinal cord" J. Neurosci., 1999, 19(8), pp. 3171-3182.
Watson, "Rethinking the mood and anxiety disorders: a quantitative hierarchical model for DSM-V", J Abnorm Psychol, Nov. 1, 2005, 114(4), 522-536.
Whitman et al., "Discovery of a Potent, CNS-Penetrant Orexin Receptor Antagonist Based on an N,N-Disubstituted-1, 4-diazepane Scaffold that Promotes Sleep in Rats", Chem Med Chem, Jul. 2009, 4, 1069-1074.
Winrow et al., "Discovery and development of orexin receptor antagonists as therapeutics for insomnia", British Journal of Pharmacology, Jan. 2014, 171, 283-293.
Winrow, C. J., "Orexin receptor antagonism prevents transcriptional and behavioral plasticity resulting from stimulant exposure" Neuropharmacology 2010, 58(1):pp. 185-194.
Winsky-Sommerer et al., "Interaction between the corticotropin-releasing factor system and hypocretins (orexins): a novel circuit mediating stress response", J Neuroscience, Dec. 2004, 24(50), 11439-11448.
Yamanaka et al.", Orexins activate histaminergic neurons via the orexin 2 receptor", Biochem. Biophys. Res. Comm., Feb. 2002, 290 (4), 1237-1245.
Yeoh et al. "Orexin antagonists for neuropsychiatric disease: progress and potential pitfalls", Frontiers in Neuroscience, Feb. 25, 2014, 8, Article No. 36, 12 pages.
Mercer et al., "Discovery of 2,5-diarylnicotinamides as selective orexin-2 receptor antagonists (2-SORAs)", Bioorganic & Medicinal Chemistry Letters, Dec. 2013, 23, 6620-6624.
Micheli et al., "2-Methyl-3-furany1-4H-1,2,4-triazol-3-ylthioamides: A new class of selective orexin 2 antagonists", Bioorganic & Medicinal Chemistry Letters, Nov. 2010, 20, 6405-6407.
Michelson et al., "Safety and efficacy of suvorexant during 1-year treatment of insomnia with subsequent abrupt treatment discontinuation: a phase 3 randomised, double-blind, placebo-controlled trial", The Lancet, May 2014, 13, 461-471.
Mignot et al. "Complex HLA-DR and-DQ interactions confer risk of narcolepsy-cataplexy in three ethnic groups", Am. J. Hum. Genet. 2001, 68 (3), pp. 686-699.
Mignot et al., "Narcolepsy and the HLA System", New England J. Med., Mar. 2001, 344 (9), 692.
Minerva Neurosciences Inc., Form 10-K, Mar. 14, 2016.
Minerva Neurosciences Inc., Form 10-K, Mar. 26, 2015.
Minerva Neurosciences Inc., Form 10-Q, Aug. 4, 2016.

(56) References Cited

OTHER PUBLICATIONS

Minerva Neurosciences Inc., Form 10-Q, Aug. 5, 2015.
Minerva Neurosciences Inc., Form 10-Q, Aug. 7, 2014.
Minerva Neurosciences Inc., Form 10-Q, May 3, 2016.
Minerva Neurosciences Inc., Form 10-Q, May 7, 2015.
Minerva Neurosciences Inc., Form 10-Q, Nov. 3, 2016.
Minerva Neurosciences Inc., Form 10-Q, Nov. 5, 2015.
Minerva Neurosciences Inc., Form 10-Q, Nov. 6, 2014.
Minerva Neurosciences Inc., Form 424B3, Jun. 16, 2015.
Minerva Neurosciences Inc., Form 424B4, Jul. 1, 2014.
Minerva Neurosciences Inc., Form 424B5, Jun. 14, 2016.
Minerva Neurosciences Inc., Form 424B5, Jun. 13, 2016.
Minerva Neurosciences Inc., Form 8-K, Aug. 7, 2014.
Minerva Neurosciences Inc., Form 8-K, Dec. 18, 2015.
Minerva Neurosciences Inc., Form 8-K, Dec. 29, 2015.
Minerva Neurosciences Inc., Form 8-K, Dec. 5, 2016.
Minerva Neurosciences Inc., Form 8-K, Dec. 9, 2015.
Minerva Neurosciences Inc., Form 8-K, Feb. 1, 2016.
Minerva Neurosciences Inc., Form 8-K, Feb. 22, 2016.
Minerva Neurosciences Inc., Form 8-K, Feb. 27, 2017.
Minerva Neurosciences Inc., Form 8-K, Jan. 11, 2016.
Minerva Neurosciences Inc., Form 8-K, Jan. 20, 2017.
Minerva Neurosciences Inc., Form 8-K, Jan. 21, 2015.
Minerva Neurosciences Inc., Form 8-K, Jan. 6, 2017.
Minerva Neurosciences Inc., Form 8-K, Jun. 13, 2016.
Minerva Neurosciences Inc., Form 8-K, Jun. 14, 2016.
Minerva Neurosciences Inc., Form 8-K, Jun. 16, 2015.
Minerva Neurosciences Inc., Form 8-K, Jun. 6, 2016.
Minerva Neurosciences Inc., Form 8-K, Mar. 11, 2016.
Minerva Neurosciences Inc., Form 8-K, Mar. 13, 2015.
Minerva Neurosciences Inc., Form 8-K, Mar. 26, 2015.
Minerva Neurosciences Inc., Form 8-K, Mar. 3, 2015.
Minerva Neurosciences Inc., Form 8-K, May 26, 2016.
Minerva Neurosciences Inc., Form 8-K, Nov. 6, 2014.
Minerva Neurosciences Inc., Form 8-K, Oct. 26, 2016.
Minerva Neurosciences Inc., Form 8-K, Sep. 24, 2015.
Minerva Neurosciences Inc., Form 8-K, Sep. 26, 2016.
Minerva Neurosciences Inc., Form DEF-14A, Apr. 29, 2016.
Minerva Neurosciences Inc., Form S-1, Apr. 9, 2014.
Minerva Neurosciences Inc., Form S-1, Jun. 10, 2014.
Minerva Neurosciences Inc., Form S-1A, Jun. 30, 2014.

Minerva Press Release, Feb. 1, 2016.
Minerva Press Release, Jan. 11, 2016.
Psychiatria et Neurologia Japonica, Choosing the Adequate Antidepressant Focusing on Efficacy, Tolerability and its Predictors, 2012, vol. 114, No. 5, p. 589-600.
"A randomized, placebo-controlled, 2-way crossover, double-blind study to evaluate the efficacy, safety and tolerabili of JNJ-42847922 in subjects with insomnia disorder without psychiatric comorbidity," Centrale Commissie Mensgebonden Onderzoek, dossier #NL54083.056.15, Jul. 28, 2015.
"A double-blind, randomized, controlled, 3-way crossover, pilot study to evaluate the duration of effects on simulated car driving and cognitive performance after a single dose of JNJ-42847922, zolpidem and placebo in healthy subjects," Centrale Commissie Mensgebonden Onderzoek, dossier #NL55279.056.15, Nov. 10, 2015.
"A single dose, 4-way crossover, double-blind, placebo-controlled, randomized study to investigate the effect ofJNJ-42847922 on polysomnography (PSG) measures in subjects with major depressive disorder with insomniawho are stably treated with antidepressants," Centrale Commissie Mensgebonden Onderzoek, dossier # NL47595.056.13, Jun. 18, 2014.
"An Exploratory Multicenter, Double-Blind, Diphenhydramine- and Placebo-Controlled Safety, Efficacy and Biomarker Study with JNJ-42847922 in Subjects with Major Depressive Disorder," Centrale Commissie Mensgebonden Onderzoek, dossier # NL53141.056.15, Aug. 17, 2015.
"An exploratory, multicenter, placebo-controlled, randomized, double-blind study to investigate the antidepressantmechanism-of-action of JNJ-42847922 in subjects with major depressive disorder," Centrale Commissie Mensgebonden Onderzoek, dossier # NL63487.056.17, Nov. 23, 2017.
Study NCT02067299; A Single Dose, 4-way Crossover, Placebo-controlled, Randomized Study to Investigate the Effect of JNJ-42847922 on Polysomnography (PSG) Measures in Subjects With Major Depressive Disorder With Insomnia Who Are Stably Treated With Antidepressants, submitted Feb. 19, 2014 (v1).
Nutt, D. et al., Sleep disorders as core symptoms of depression. Dialogues in Clinical Neuroscience, Sep. 30, 2008, vol. 10, No. 3, pp. 329-336.
Ohayon MM. Prevalence of DSM-IV diagnostic criteria of insomnia: distinguishing insomnia related to mental disorders from sleep disorders. J Psychiatr Res. 1997;31:333-346.

\* cited by examiner

TREATMENT = Compound A 20 mg Solid Formulation Semi-fasted

TREATMENT = Compound A 20 mg Solid Formulation Semi-fasted

METHODS OF TREATING DEPRESSION USING OREXIN-2 RECEPTOR ANTAGONISTS

CROSS-REFERENCE TO RELATED APPLICATIONS

This application is a continuation of U.S. patent application Ser. No. 15/454,628, filed Mar. 9, 2017, which claims priority to U.S. Provisional Patent Application No. 62/306,487, filed Mar. 10, 2016, which are both incorporated by reference herein.

TECHNICAL FIELD

The present disclosure is directed to, among other things, methods for the treatment of depression.

BACKGROUND

Orexins (also known as hypocretins) are neuropeptides expressed by neurons in the perifornical area, the dorsomedial hypothalamus and the lateral hypothalamus (de Lecea et al., 1998; Proc. Natl. Acad. Sci. U.S.A. 95, 322-327; Sakaurai et al, 1998, Cell 92, 573-585). Orexinergic neurons project to many areas of the brain including other hypothalamic nuclei, the midline paraventricular thalamus, brain stem nuclei, the ventral tegmental area and nucleus accumbens shell. (Peyron et al., 1998, J. Neurosci. 18, 9996-10016) Orexin neuropeptides, classified as either orexin-A or orexin-B, bind to the seven transmembrane G-protein coupled receptors orexin-1 (OX1R) and orexin-2 (OX2R) (de Lecea et al., 1998; Proc. Natl. Acad. Sci. U.S.A. 95, 322-327; Sakaurai et al, 1998, Cell 92, 573-585). While orexin-A is non-selective for OX1R and OX2R, orexin-B shows higher affinity for OX2R (Sakaurai et al, 1998, Cell 92, 573-585). Orexin receptor antagonists are classified as single orexin receptor (SORAs) or dual receptor antagonists (DORAs).

Hypothalamic orexinergic neurons expressing discharge during active wake, are virtually silent during non-rapid eye movement sleep and show transient discharges during rapid eye movement sleep (Lee, 2005, J. Neuroscience 25(8): 6716-6720; Takahashi, 2008, Neuroscience, 153: 860-870). This activity pattern supports the notion that the orexins are endogenous, potent, arousal (wakefulness)-promoting peptides. Studies using single unit recordings also show that OX-containing neurons are preferentially activated during rewarding appetitive behaviors (Hassani et al., 2016. J Neuroscience 36(5): 1747-1757). However, orexins are also hypothesized to play a role in excessive arousal (e.g. hypervigilance, anxiety, somatic tension, agitation and/or excessive rumination) which occurs in subsets of patients with mood disorders. To date, it is believed that intrinsic antidepressant activity of a selective OXR2 antagonist has not been explored clinically.

As is known in the art, clinically significant improvement in symptoms of depression in subjects diagnosed with Major Depressive Disorder (MDD) may take 4-6 weeks after the initiation of treatment with currently available antidepressants. Therefore, it is not expected that MDD subjects would benefit from shorter periods of antidepressant therapy, especially 2 weeks or less. There remains a high, unmet medical need to provide an effective treatment for depression.

SUMMARY

The general description and the following detailed description are exemplary and explanatory only and are not restrictive of the disclosure, as defined in the appended claims. Other aspects of the present disclosure will be apparent to those skilled in the art in view of the detailed description of the disclosure as provided herein.

In one aspect, methods of treating a subject suffering from or diagnosed with depression are provided. These methods comprise administering to a subject in need of such treatment an effective amount of a compound of formula (I), or a pharmaceutically acceptable salt thereof, wherein $R^1$-$R^4$ are defined herein, and wherein the compound of formula (I) is administered prior to sleep.

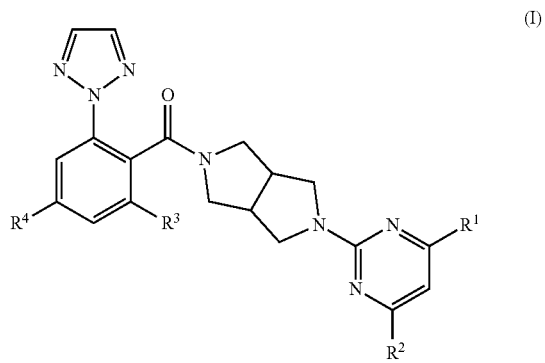

In another aspect, the subject treated according to the methods described herein is not suffering from or diagnosed with an insomnia disorder.

In a further aspect, the compound of formula (I) is administered at night according to the methods described herein.

BRIEF DESCRIPTION OF THE FIGURES

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The summary, as well as the following detailed description, is further understood when read in conjunction with the appended figures.

DETAILED DESCRIPTION OF ILLUSTRATIVE EMBODIMENTS

I. Definitions

Figure 1:
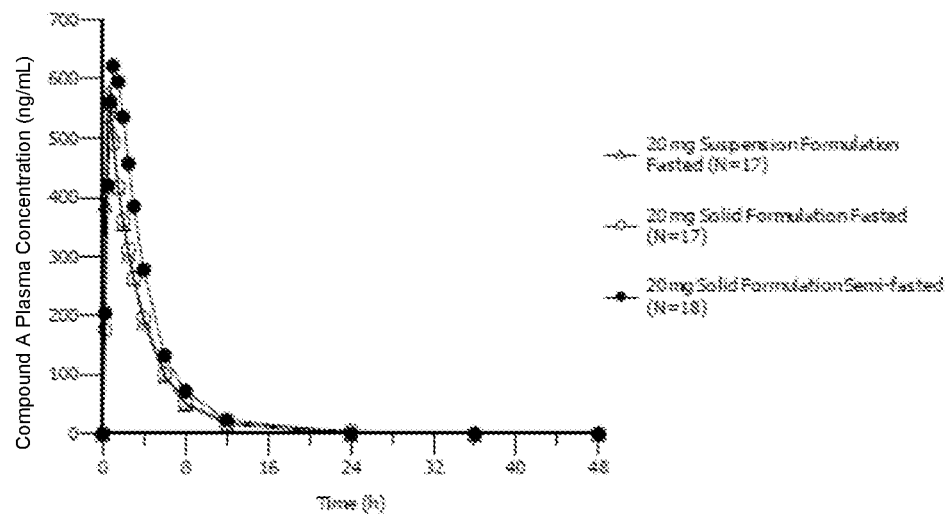
FIGS. 1-2 are the mean plasma concentration-time profiles for [5(4,6-dimethyl-pyrimidin-2-yl)-hexahydro-pyrrolo[3,4-c]pyrrol-2-yl]-(2-fluoro-2-[1,2,3]triazol-2-yl-phenyl)-methanone (Compound A) formulations.
Figure 2:
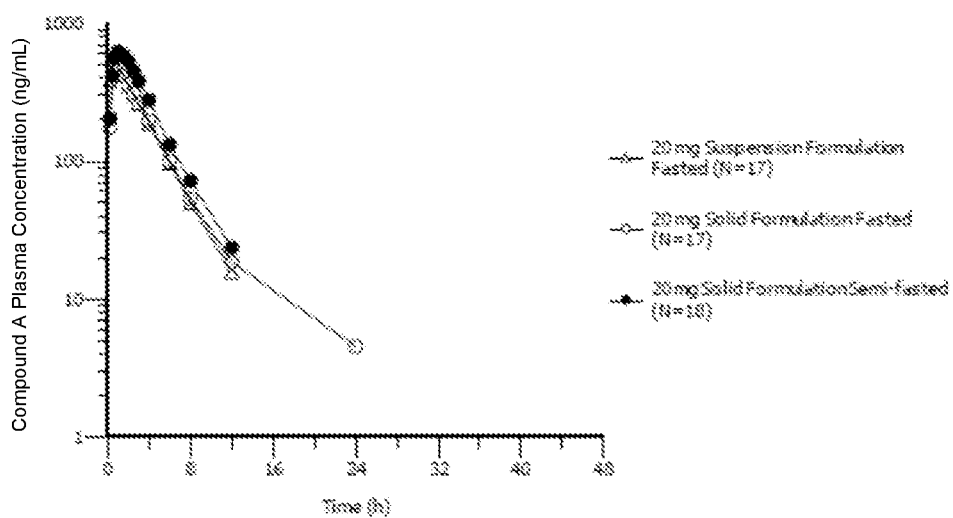
Figure 3:
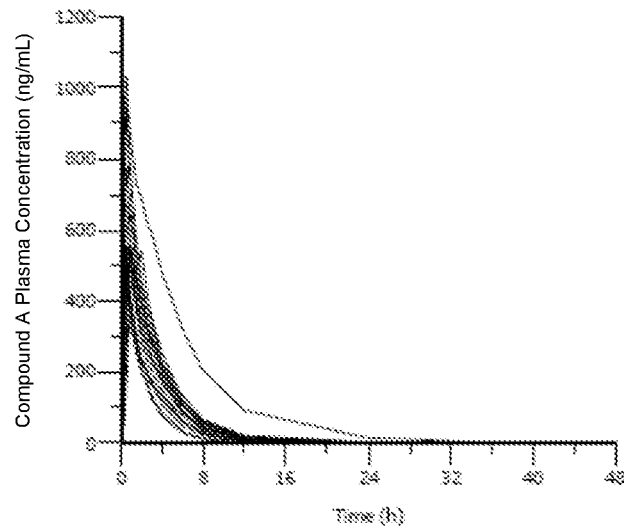
FIGS. 3-8 are the composite plasma concentration-time profiles for Compound A formulations.
Figure 4:
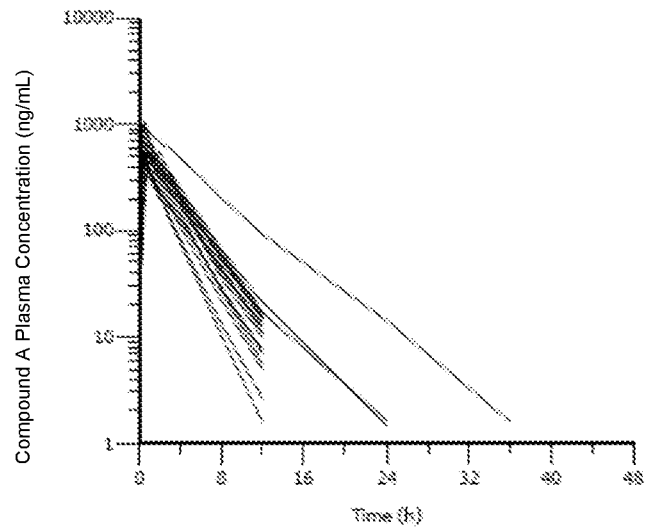
Figure 5:
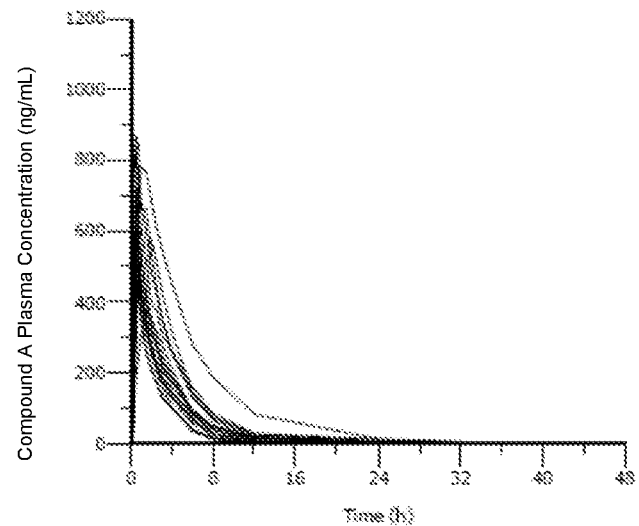
Figure 6:
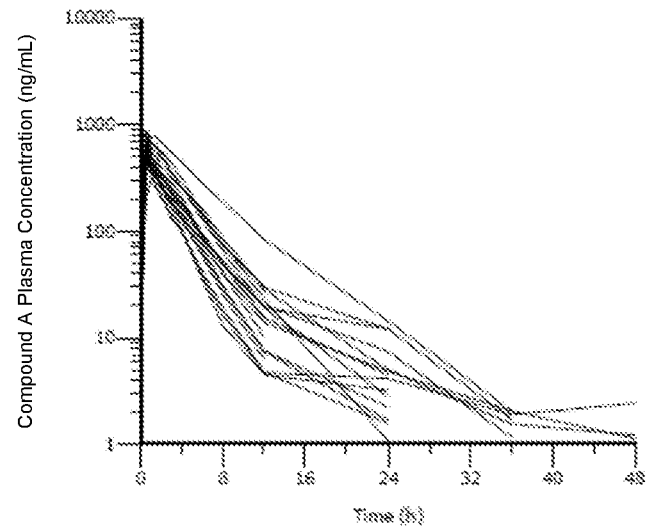
Figure 7:
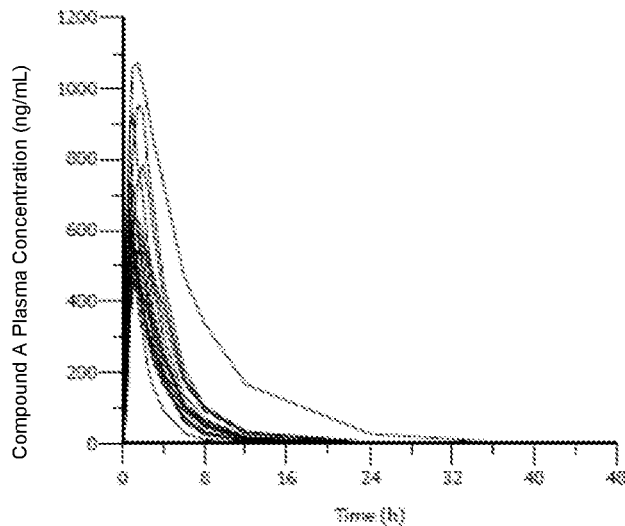
Figure 8:
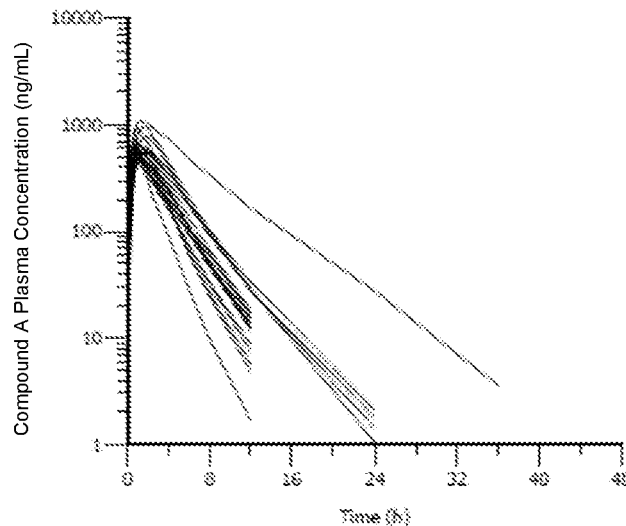
Figure 9:
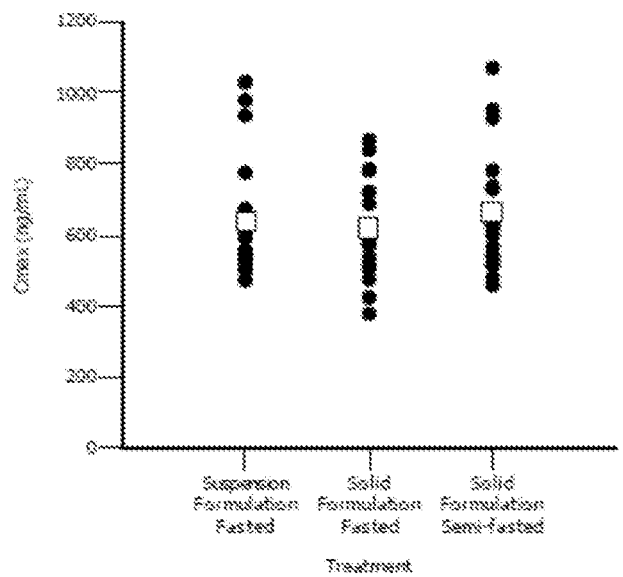
FIGS. 9-11 are the individual and mean plasma pharmacokinetic parameters versus treatment plots for Compound A formulations.
Figure 10:
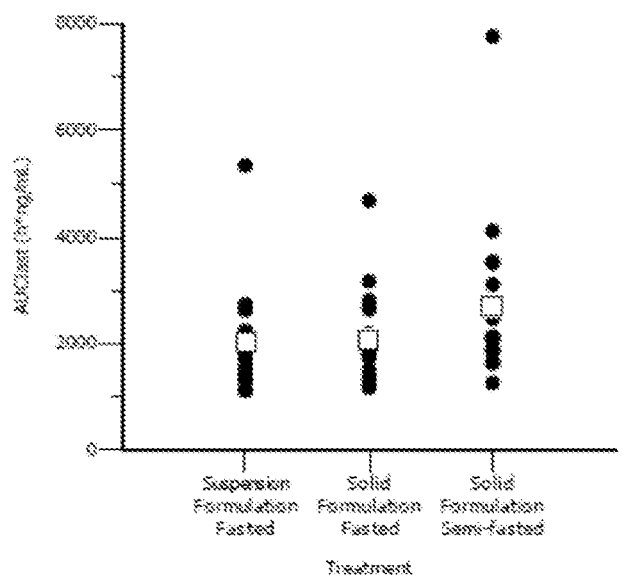
Figure 11:
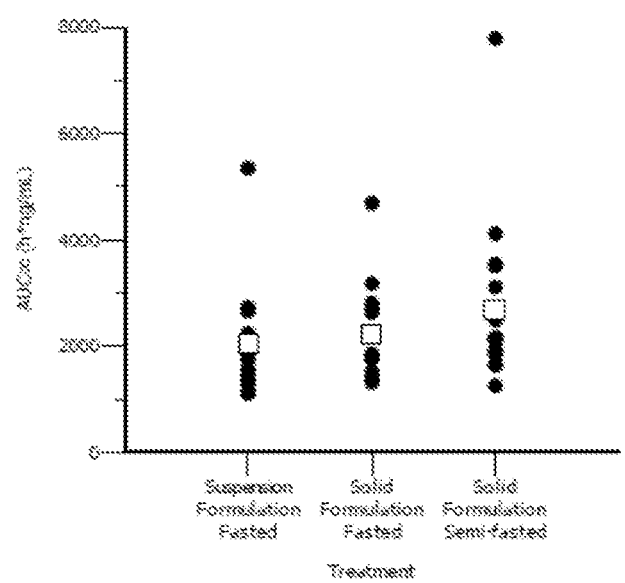

The term "depression" includes major depressive disorder, persistent depressive disorder, depression associated with bipolar disorder (aka bipolar depression), seasonal affective disorder, psychotic depression, postpartum depression, premenstrual dysphoric disorder, situational depression, anhedonia, melancholy, mid-life depression, late-life depression, depression due to identifiable stressors, treatment resistant depression, or combinations thereof. In certain embodiments, the depression is major depressive disorder. In other embodiments, the major depressive disorder is with melancholic features or anxious distress.

The methods described herein are useful in the treatment of the core (or psychic) symptoms of depression. These symptoms include depressed mood and loss of interest or pleasure in nearly all activities.

The term "sleep onset" refers to the transition from wakefulness into non-rapid eye movement (NREM) sleep; and "sleep" generally refers to non-rapid eye movement (NREM) or rapid eye movement (REM) sleep.

The term "awake" describes a reasonably alert state of consciousness characterized by alpha and beta waves as detected by electroencephalogram, voluntary rapid eye movements and/or eye blinks. In other embodiments, an awake state may be characterized as the absence of NREM or REM sleep.

The term "night" includes the period of time from sunset to sunrise, occurring once each twenty-four hours. In some embodiments, night refers to a timeframe in a twenty-four period in a day that precedes sleep by a subject.

An "insomnia disorder" refers to a diagnosis using criteria found in the American Psychiatric Association's fifth edition of the Diagnostic and Statistical Manual of Mental Disorders (DSM-V) and the Third Edition of the World Health Organization's International Classification of Sleep Disorders (ICSD-3). In some embodiments, an "insomnia disorder" includes the difficulty initiating or maintaining sleep and waking too early and/or obtaining non-restorative sleep, where the sleep difficulty results in some form of daytime impairment.

Some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the terms "treating", "treatment" and the like, shall include the management and care of a subject or patient (preferably mammal, more preferably human) for the purpose of combating a disease, condition, or disorder and include the administration of a compound described herein to prevent the onset of the symptoms or complications, alleviate the symptoms or complications, or eliminate the disease, condition, or disorder. Similarly, "treatment" is used to encompass (a) reduction in the frequency of one or more symptoms; (b) reduction in the severity of one or more symptoms; (c) the delay or avoidance of the development of additional symptoms; and/or (d) delay or avoidance of the development of the disorder or condition, or any combination thereof.

As used herein, unless otherwise noted, the terms "subject" and "patient" may be used interchangeably and refer to an animal, preferably a mammal, most preferably a human, who has been the object of treatment, observation or experiment. In some embodiments, the subject or patient has experienced and/or exhibited at least one symptom of the disease or disorder to be treated and/or prevented. One skilled in the art will further recognize that the methods of treatment are directed to subjects or patients in need of such treatment, prevention or dosing regimen, more particularly to subjects or patients diagnosed with or exhibiting at least one symptom of depression (preferably, meeting the criteria for major depressive disorder or episode) regardless of type or underlying cause. In further embodiments, the subject is not suffering from or diagnosed with an insomnia disorder.

One skilled in the art will recognize that wherein methods of prevention are described, a subject in need thereof (i.e. a subject in need of prevention) shall include any subject who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of having new episodes of depression (and therefore in need of secondary prevention or preventive treatment) as a consequence of the subject's medical history, including, but not limited to, family history, pre-disposition, co-existing (comorbid) disorders or conditions, genetic testing, and the like.

Further, some of the quantitative expressions herein are recited as a range from about value X to about value Y. It is understood that wherein a range is recited, the range is not limited to the recited upper and lower bounds, but rather includes the full range from about value X through about value Y, or any value or range of values therein.

As used herein, the terms "including", "containing" and "comprising" are used herein in their open, non-limiting sense.

II. The Compounds

As discussed above, the compounds described herein are orexin-2 antagonists and may be used in the treatment of depression. In some embodiments, the compounds are administered such that they have a time to maximal plasma concentration of less than about 3 hours, less than about 2 hours, and preferably less than about 1 hour, i.e., less than about 45 minutes, less than about 30 minutes, less than about 15 minutes, among others. In other embodiments, the compound has an elimination half-life of about 4 hours and typically less than about 4 hours. For example, certain compounds of the present disclosure have a half-life of about 2 to about 3 hours, e.g., about 2 hours, about 2.1 hours, about 2.2 hours, about 2.3 hours, about 2.4 hours, about 2.5 hours, about 2.6 hours, about 2.7 hours, about 2.8 hours, or about 2.9 hours to about 3 hours. Given the short half-life, the amount of the compound remaining in the subject upon waking is typically below the threshold required for pharmacodynamic effect. For example, the compounds of the present disclosure typically have a pharmacodynamic effect from a dose level greater than about 5 mg.

In certain embodiments, the compound has the structure of formula (I):

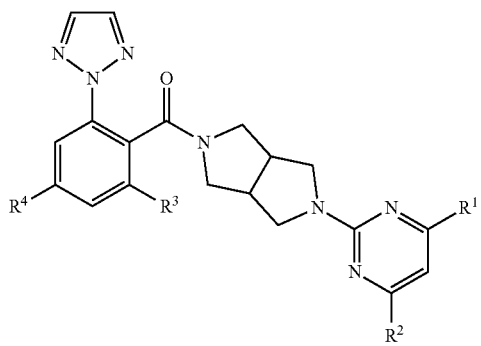

(I)

$R^1$ is $C_{1-4}$ alkyl. In some embodiments, $R^1$ is $CH_3$.
$R^2$ is $C_{1-4}$ alkyl. In some embodiments, $R^2$ is $CH_3$.
$R^3$ is H or halogen. In some embodiments, $R^3$ is halogen. In other embodiments, $R^3$ is fluorine. In further embodiments, $R^3$ is H.
$R^4$ is H or $C_{1-4}$ alkoxy. In some embodiments, $R^4$ is H. In further embodiments, $R^4$ is $C_{1-4}$alkoxy. In other embodiments, $R^4$ is methoxy.

"Alkyl" refers to a straight- or branched-chain alkyl group having from 1 to 12 carbon atoms in the chain. Examples of alkyl groups include methyl, ethyl, n-propyl, isopropyl, butyl, isobutyl, sec-butyl, tert-butyl and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 5 to 7 ring atoms per carbocycle. Illustrative examples of cycloalkyl groups include the following entities, in the form of properly bonded moieties:

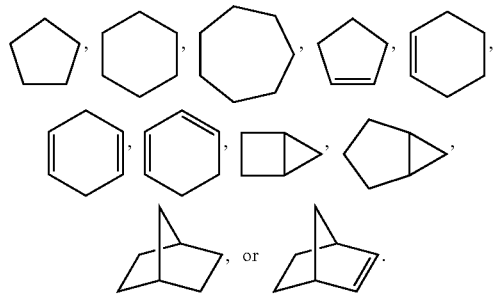

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

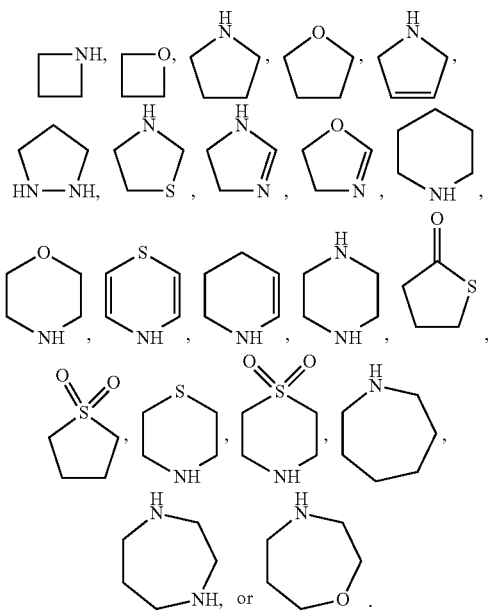

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

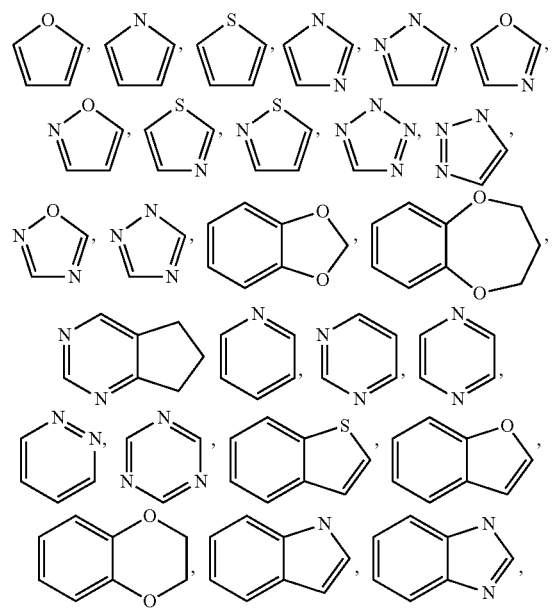

-continued

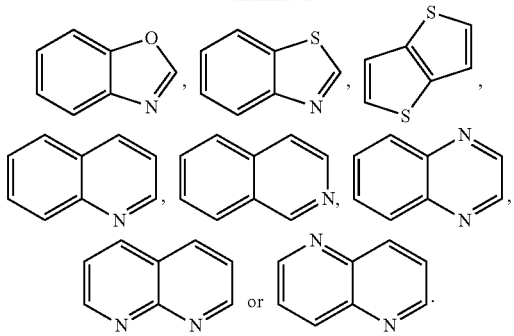

Those skilled in the art will recognize that the species of heteroaryl, cycloalkyl, and heterocycloalkyl groups listed or illustrated above are not exhaustive, and that additional species within the scope of these defined terms may also be selected.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, and so on.

"Halogen" represents chlorine, fluorine, bromine or iodine.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

The nomenclature "$C_{i-j}$" with j>i, when applied herein to a class of substituents, is meant to refer to embodiments for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any formula given herein is intended to represent a compound having a structure depicted by the structural formula as well as certain variations or forms. In particular, a compound of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The compounds may include those described in U.S. Pat. No. 8,653,263 and US Patent Publication No. 2014/0171430, both of which are incorporated herein by reference. In some embodiments, the compound is 5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone or a pharmaceutically acceptable salt thereof. In other embodiments, the compound is 5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone. In further embodiments, the compound is 5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone hydrochloride. In yet other embodiments, the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone or a pharmaceutically acceptable salt thereof. In still further embodiments, the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone. In certain embodiments, the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone hydrate. In other embodiments, the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone hydrochloride hydrate. In further embodiments, the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone hydrobromide hydrate.

Additionally, any formula given herein is intended to refer also to hydrates, solvates, and polymorphs of such compound, and mixtures thereof, even if such forms are not listed explicitly. A compound of Formula (I) or pharmaceutically acceptable salts of a compound of Formula (I) may be obtained as solvates. Solvates include those formed from the interaction or complexation of a compound with one or more solvents, either in solution or as a solid or crystalline form. In some embodiments, the solvent is water and then the solvates are hydrates. In addition, crystalline forms of a compound of Formula (I) or pharmaceutically acceptable salts of a compound of Formula (I) may be obtained as co-crystals. In certain embodiments, a compound of Formula (I) is obtained in a crystalline form. In other embodiments, a crystalline form of a compound of Formula (I) is cubic in nature. In other embodiments, pharmaceutically acceptable salts of compounds of Formula (I) are obtained in a crystalline form. In still other embodiments, compounds of Formula (I) are obtained in one of several polymorphic forms, as a mixture of crystalline forms, as a polymorphic form, or as an amorphous form. In other embodiments, a compound of Formula (I) converts in solution between one or more crystalline forms and/or polymorphic forms.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorus, fluorine, and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or an $I^{123}$ for SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds described herein and prodrugs thereof can generally be prepared by carrying out the procedures disclosed in the schemes or in the examples and preparations described below by substituting a readily available isotopically labeled reagent for a non-isotopically labeled reagent.

Also included are pharmaceutically acceptable salt of a compound of Formula (I) and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn, "Trends in Active Pharmaceutical Ingredient Salt Selection based on Analysis of the Orange Book Database", J. Med. Chem., 2007, 50:6665-72, S. M. Berge, "Pharmaceutical Salts", J Pharm Sci., 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

The desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid, or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary, or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Pharmaceutically acceptable prodrugs of a compound of Formula (I) and treatment methods employing such pharmaceutically acceptable prodrugs are also contemplated. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three, or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher, Adv. Drug Delivery Rev. 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson, J. Med. Chem. 1996, 39(I),10-18.

Free amines can also be derivatized as amides, sulfonamides, or phosphonamides. All of these prodrug moieties may incorporate groups including ether (—O—), amine (—N—), and carboxylic acid (COO—) functionalities.

III. Compositions

The compounds described herein, including the compounds of formula (I), may be formulated as a pharmaceutical composition to administration to a subject. Accordingly, a pharmaceutical composition may comprise (a) an effective amount of at least one compound described herein and (b) a pharmaceutically acceptable excipient. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds described herein may be prepared using suitable pharmaceutical excipients and compounding techniques known or that become available to those skilled in the art. The compositions may be administered in the inventive methods by a suitable route of delivery, e.g., oral, parenteral, rectal, topical, ocular routes, or by inhalation.

The preparation may be in the form of tablets, capsules, sachets, dragees, powders, granules, lozenges, powders for reconstitution, or liquid preparations. In some embodiments, the compositions are formulated for intravenous infusion, topical administration, or oral administration. In certain embodiments, the compositions are formulated for immediate release.

For oral administration, the compounds can be provided in the form of tablets or capsules, or as a solution, emulsion, or suspension. In certain embodiments, the compounds may be taken with food.

Oral tablets may include a compound mixed with pharmaceutically acceptable excipients such as inert fillers, diluents, disintegrating agents, binding agents, lubricating agents, sweetening agents, flavoring agents, coloring agents, glidants and preservative agents. Suitable inert fillers include sodium and calcium carbonate, sodium and calcium phosphate, lactose, lactose monohydrate, starch, sugar, glucose, methyl cellulose, magnesium stearate, mannitol, sorbitol, hypromellose, and the like. Exemplary liquid oral excipients include ethanol, glycerol, water, and the like. Starch, polyvinyl-pyrrolidone, sodium starch glycolate, microcrystalline cellulose, crospovidone (cross-linked polyvinyl N-pyrrolidone or PVP), and alginic acid are suitable disintegrating agents. Binding agents may include hypromellose (hydroxypropyl methylcellulose or HPMC), starch and gelatin. The lubricating agent, if present, may be magnesium stearate, stearic acid, or talc. The glidant, if present, may be silica (Sift) such as colloidal silica. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, the compound may be mixed with a solid, semi-solid, or liquid diluent. Soft gelatin capsules may be prepared by mixing the compound with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups or may be lyophilized or presented as a dry product for reconstitution with water or other suitable vehicle before use. Such liquid compositions may optionally contain pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds described herein may also be administered by non-oral routes. For example, the compounds may be formulated for rectal administration. For parenteral use, including intravenous, intramuscular, or intraperitoneal routes, the compound may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of the compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compound may utilize a patch formulation to affect transdermal delivery.

Compounds may alternatively be administered by inhalation, via the nasal or oral routes, e.g., in a spray formulation also containing a suitable carrier.

VI. Methods of Treating Depression

As described herein, the inventors found a surprising, robust antidepressant effect when using the compounds described on subjects diagnosed with depression. Although not intending to be limited by theory, it is believed that because the activity of orexin containing neurons is negligible during sleep (typically at night), the antidepressant efficacy of the compounds discussed herein is surprising. As disclosed herein, administration prior to sleep (typically at night) of the compounds of the disclosure is associated with statistically significant antidepressant efficacy, with the efficacy not related to the effect on sleep items.

Accordingly, methods of treating a subject suffering from or diagnosed with depression are provided. These methods comprise administering to a subject in need of such treatment an effective amount of a compound described herein. In certain embodiments, the compound is of formula (I).

The compound is preferably administered once daily and is administered to the subject prior to sleep. For example, the compound is administered within about 2 hours of sleep, within about 1 hour, or within about 30 minutes before sleep.

In other embodiments, the compound is administered at least about 4 hours before the subject wakes or intends to wake from sleep, including about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, or about 12 hours before the subject wakes or intends to wake from sleep. In certain embodiments, the compound is administered at least 6 hours to about 12 hours before the subject wakes or intends to wake from sleep. In preferred embodiments, the compound is administered at night.

After administration of the compound, the compound undergoes at least one half-life before the subject wakes from sleep. In other embodiments, the compound undergoes at least two half-lives, and preferably at least three half-lives before the subject wakes from sleep.

Desirably, the compound is below the threshold required for pharmacodynamic effect after about 6 to about 8 hours after administration of the compound. This differs from antidepressants in the art which are designed to achieve a steady state concentration of the antidepressant in the patient. The methods described herein differ in that after one to eight hours of administration of the drug, the concentration of the drug will fall below pharmacodynamic levels and remain at those levels for the remainder of the 24-hour treatment period until the next dose of drug is administered.

Therapeutically effective amounts for the compounds described herein include amounts that elicit the biological or medicinal response in a tissue system, animal or human that is being sought by a researcher, veterinarian, medical doctor, or other clinician, which includes alleviation of the symptoms of the disease or disorder being treated. Optimal dosages to be administered may be readily determined by those skilled in the art, and may vary with the mode of administration, the strength of the preparation and the advancement of the disease condition. Such factors including the particular patient being treated, including patient's sex, age, weight, diet, time of administration and concomitant diseases, among others. In certain embodiments, the effective amount of each dose of the compounds described herein is about 0.001 to about 200 mg of compound per kg of subject's body weight per day, about 0.05 to 100 mg/kg/day, or about 1 to 35 mg/kg/day, in single or divided dosage units (examples of such dosage units include 2.5 mg, 5 mg, 10 mg, and 20 mg tablets). For a 70 kg human, an illustrative range for a suitable dosage amount is from about 0.05 to about 7 g/day, or about 0.2 to about 2.5 g/day.

The effective amount of the compound described herein may also be described without reference to the weight of the subject. Accordingly, the effective amount of the compound is about 10 to about 60 mg. In some embodiments, the effective amount of the compound is about 10 mg, about 15 mg, about 20 mg, about 25 mg, about 30 mg, about 35 mg, or about 40 mg, or within a range defined by any two of these values.

The effective amount of the compound may be administered in a single daily dose. In further embodiments, the compound is administered daily and one or more symptoms of the depression is reduced or ameliorated within about 11 days of a first administration, i.e., day 1.

Frequency adjustment can be accomplished by a one-time switch in frequency or may be determined over two or more administrations. By doing so, the attending physician or the like may determine an optimal frequency for administration and thereby tailor the administration to the patient.

Also contemplated by these methods is the administration of rescue doses of the compounds described herein. The term "rescue dose" as used herein refers to one or more additional doses of a compound described herein in addition to the regularly prescribed dose. The amount of a compound described herein in the rescue dose may be determined by the prescribing physician or clinician and will depend on any of the factors discussed herein. In certain embodiments, the rescue dose of a compounds described herein is the same as the effective dose used during the normal administration schedule. In other embodiments, the rescue dose differs from the effective dose used during the normal administration schedule.

One skilled in the art will recognize that in the methods described herein, the maintenance of the response in a patient may be determined by for example, a clinician, physician, psychiatrist, psychologist, or other suitable medical professional. Additionally, maintenance of the antidepressant response may be established by for example, an absence of relapse of the depression (or one or more symptoms of the depression), an absence of the need for additional or alternate treatment(s) for the depression, or an absence of the worsening of the depression. The physician or attending clinician may utilize any technique known in the art including, without limitation, general patient evaluation, diagnostic questionnaires, and evaluations such as the Clinical Global Impression-Severity (CGI-S) scale, EuroQol; 5 dimension; 5 level (EQ-5D-5L), Patient Health Questionnaire-9 Item (PHQ-9), Sheehan Disability Scale (SDS), Inventory of Depressive Symptomatology-Clinician rated, 30-item scale (IDS-$C_{30}$), Montgomery-Asberg Depression Rating Scale (MADRS) questionnaire, Hamilton rating scale for depression (HAM-D or HDRS) Beck Scale for Depression, or Quick Inventory of Depressive Symptomology (QIDS). The frequency may be evaluated and/or changed if the score from one or more of the above-noted scales or questionnaire changes.

In addition, the compounds may be used in combination with additional active ingredients in the treatment of the above conditions. The additional active ingredients may be administered simultaneously, separately or sequentially. In some embodiments, the additional active ingredients are effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of a compound herein), decrease one or more side effects, or decrease the required dose of the compound described herein or additional active agent. In certain embodiments, the additional active ingredient is an antidepressant. In other embodiments, the additional active ingredient is a monoaminergic antidepressant.

Accordingly, the compound of formula (I) may be used in combination with a second antidepressant. The second antidepressant may be a conventional drug used to combat depression such as N-methyl-D-aspartate receptor antagonists, norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), noradrenergic and specific serotonergic antidepressants (NaSSAs), corticotropin releasing factor (CRF) antagonists, alpha-adrenoreceptor antagonists and atypical antidepressants. In some embodiments, the N-methyl-D-aspartate (NMDA) receptor antagonist is ketamine including its racemates esketamine, arketamine, or combinations thereof. In further embodiments, the norepinephrine reuptake inhibitor includes amitriptyline, clomipramine, doxepin, imipramine, trimipramine, amoxapine, desipramine, maprotiline, nortriptyline, protriptyline, reboxetine, or pharmaceutically acceptable salts thereof. In other embodiments, the selective serotonin reuptake inhibitor includes fluoxetine, fluvoxamine, paroxetine, sertraline, or pharmaceutically acceptable salts thereof. In further embodiments, the monoamine oxidase inhibitor includes isocarboxazid, phenelzine, tranylcypromine, selegiline and pharmaceutically acceptable salts thereof. In yet other embodiments, the reversible inhibitor of monoamine oxidase includes moclobemide or pharmaceutically acceptable salts thereof. In still further embodiments, the serotonin and noradrenaline reuptake inhibitor includes venlafaxine or pharmaceutically acceptable salts thereof. In other embodiments, the atypical antidepressant includes bupropion, lithium, nefazodone, trazodone, viloxazine, sibutramine, or pharmaceutically acceptable salts thereof. In yet further embodiments, the second antidepressant includes adinazolam, alaproclate, amineptine, amitriptyline/chlordiazepoxide combination, atipamezole, azamianserin, bazinaprine, befuraline, bifemelane, binodaline, bipenamol, brofaromine, bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, monirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, tofenacin, tofisopam, toloxatone, tomoxetine, veralipride, viqualine, zimelidine zometapine, or pharmaceutically acceptable salts thereof; or St. John's wort herb, *Hypericum perforatum*, or extracts thereof.

In some embodiments, the compound of formula (I) is co-administered with esketamine. In further embodiments, the compound of formula (I) is administered separately from esketamine such as, e.g., sequentially. The compound of formula (I) may be administered prior or subsequent to esketamine.

V. Kits

Also described herein are kits for administering one or more compounds described herein to a patient for the treatment of depression. The representative kits include one or more dosage units comprising an effective amount of one or more compounds described herein for administration to a patient and at a given frequency.

The dosage unit may be formulated for delivery by any means. In certain embodiments, the dosage unit is formulated for oral, intravenous, intranasal, intramuscular, sublingual, transdermal, otic, or rectal delivery. In certain embodiments, the dosage unit is formulated for oral delivery.

The dosage unit may be formulated to contain any amount of a compound described herein, depending on the route of administration. Accordingly, each dosage unit may comprise the required dosage for the patient or may comprise a portion of a compound described herein which is required for a single dosage.

Also optionally included in the kits is a depression symptom rating scale questionnaire. The questionnaire may be for use by the patient alone or in combination with a physician. The questionnaire may be useful for determining the level of depression of the patient at any stage of compound administration. In one embodiment, the questionnaire is one or more of the questionnaires noted herein.

Instructions for performing the claimed methods and administering the compound may also be included in the kits described herein.

The kits may be organized to indicate a single formulation containing a compound described herein or combination of formulations, each containing a compound described herein. The composition may be sub-divided to contain appropriate quantities of a compound described herein. The unit dosage can be packaged compositions such as packeted powders, vials, ampoules, prefilled syringes, tablets, caplets, capsules, or sachets containing liquids.

The compound described herein may be a single dose or for continuous or periodic discontinuous administration. For continuous administration, a kit may include a compound described herein in each dosage unit. When varying concentrations of a compound described herein, the components of the composition containing the compound described herein, or relative ratios of the compound described herein or other agents within a composition over time is desired, a kit may contain a sequence of dosage units.

The kit may contain packaging or a container with a compound described herein formulated for the desired delivery route. The kit may also contain dosing instructions, an insert regarding the compound described herein, instructions for monitoring circulating levels of the compound, or combinations thereof. Materials for using the compound may further be included and include, without limitation, reagents, well plates, containers, markers, or labels, and the like. Such kits may be packaged in a manner suitable for treatment of a desired indication Other suitable components to include in such kits will be readily apparent to one of skill in the art, taking into consideration the desired indication and the delivery route. The kits also may include, or be packaged with, instruments for assisting with the injection/administration of the compound to the patient. Such instruments include, without limitation, an inhalant, syringe, pipette, forceps, measuring spoon, eye dropper, or any such medically approved delivery means. Other instrumentation may include a device that permits reading or monitoring reactions in vitro.

The compound may be provided in dried, lyophilized, or liquid forms. When reagents or components are provided as a dried form, reconstitution generally is by the addition of a solvent. The solvent may be provided in another packaging means and may be selected by one skilled in the art.

A number of packages or kits are known to those skilled in the art for dispensing pharmaceutical agents. In certain embodiments, the package is a labeled blister package, dial dispenser package, or bottle.

Methods for optimizing a dosage of the compound for a patient having or being predisposed to depression also are provided. These methods can include (a) administering an effective amount of the compound to the patient, (b) analyzing the effects of the compound, and (c) administering an effective amount of the compound to the patient less frequently of a defined duration.

VI. Aspects

The present disclosure comprises at least the following aspects.

Aspect 1. A method of treating a subject suffering from or diagnosed with depression, comprising administering to a subject in need of such treatment an effective amount of a compound of formula (I):

(I)

wherein, $R^1$ is $C_{1-4}$ alkyl; $R^2$ is $C_{1-4}$ alkyl; $R^3$ is H or halogen; and $R^4$ is H or $C_{1-4}$ alkoxy; or a pharmaceutically acceptable salt or hydrate thereof, wherein the compound is administered prior to sleep.

Aspect 2. The method of aspect 1 wherein the subject is not suffering from or diagnosed with an insomnia disorder.

Aspect 3. The method of any one of the preceding aspects, wherein $R^3$ is halogen.

Aspect 4. The method of any one of the preceding aspects, wherein $R^3$ is fluorine.

Aspect 5. The method of any one of the preceding aspects, wherein $R^4$ is H.

Aspect 6. The method of aspect 1 or 2, wherein $R^4$ is $C_{1-4}$alkoxy.

Aspect 7. The method of any one of aspects 1, 2, or 6, wherein $R^4$ is methoxy.

Aspect 8. The method of any one of aspects 1, 2, 6, or 7, wherein $R^3$ is H.

Aspect 9. The method of any one of the preceding aspects, wherein $R^1$ is $CH_3$.

Aspect 10. The method of any one of the preceding aspects, wherein $R^2$ is $CH_3$.

Aspect 11. The method of aspect 1 or 2, wherein the compound is 5-(4,6-dimethyl-pyrimidin-2-yl)-hexahydropyrrolo[3,4-c]pyrrol-2-yl]-(2-fluoro-6-[1,2,3]triazol-2-yl-phenyl)-methanone or a pharmaceutically acceptable salt thereof.

Aspect 12. The method of aspect 1, 2, or 11, wherein the compound is 5-(4,6-dimethyl-pyrimidin-2-yl)-hexahydropyrrolo[3,4-c]pyrrol-2-yl]-(2-fluoro-6-[1,2,3]triazol-2-yl-phenyl)-methanone.

Aspect 13. The method of aspect 1, 2, or 11, wherein the compound is 5-(4,6-dimethyl-pyrimidin-2-yl)-hexahydropyrrolo[3,4-c]pyrrol-2-yl]-(2-fluoro-6-[1,2,3]triazol-2-yl-phenyl)-methanone hydrochloride.

Aspect 14. The method of aspect 1 or 2, wherein the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone or a pharmaceutically acceptable salt thereof.

Aspect 15. The method of any one of aspects 1, 2, or 12, wherein the compound is (5-(4,6-dimethylpyrimidin-2-yl) hexahydropyrrolo[3,4-c]pyrrol-2(1H)-yl)(4-methoxy-2-(2H-1,2,3-triazol-2-yl)phenyl)methanone Aspect 16. The method of any one of aspects 1 to 3, wherein the compound is (5-(4,6-dimethylpyrimidin-2-yl) hexahydropyrrolo[3,4-c]pyrrol-2(1H)-yl)(4-methoxy-2-(2H-1,2,3-triazol-2-yl)phenyl)methanone hydrate.

Aspect 17. The method of any one of aspects 1 to 3, wherein the compound is (5-(4,6-dimethylpyrimidin-2-yl) hexahydropyrrolo[3,4-c]pyrrol-2(1H)-yl)(4-methoxy-2-(2H-1,2,3-triazol-2-yl)phenyl)methanone hydrochloride hydrate.

Aspect 18. The method of any one of aspects 1 to 3, wherein the compound is (5-(4,6-dimethylpyrimidin-2-yl) hexahydropyrrolo[3,4-c]pyrrol-2(1H)-yl)(4-methoxy-2-(2H-1,2,3-triazol-2-yl)phenyl)methanone hydrobromide hydrate.

Aspect 19. The method of any one of the preceding aspects, wherein the compound is administered at night.

Aspect 20. The method of any one of the preceding aspects, wherein the compound is administered such that it has a time to maximal plasma concentration of less than about 1 hour.

Aspect 21. The method of any one of the preceding aspects, wherein the compound has an elimination half-life of about 2 to about 3 hours.

Aspect 22. The method of any of the preceding aspects, wherein the compound is administered to the subject about at least 4 hours before the subject intends to wake from sleep.

Aspect 23. The method of any one of the preceding aspects, wherein the compound is below the threshold required for pharmacodynamic effect after about 6 to about 8 hours after administration of the compound.

Aspect 24. The method of any one of the preceding aspects, wherein the compound undergoes at least two half-lives before the subject wakes from sleep.

Aspect 25. The method of any one of the preceding aspects, wherein steady state of the compound is not achieved.

Aspect 26. The method of any one of the preceding aspects, wherein the compound is administered daily.

Aspect 27. The method of any one of the preceding aspects, wherein the compound is administered orally.

Aspect 28. The method of any one of the preceding aspects, wherein the effective amount is about 0.05 to about 100 mg/kg/day.

Aspect 29. The method of any one of the preceding aspects, wherein the effective amount is about 10 to about 40 mg.

Aspect 30. The method of any one of the preceding aspects, wherein the compound is administered daily and one or more symptoms of the depression is reduced or ameliorated within about 11 days of a first administration.

Aspect 31. The method of any one of the preceding aspects, wherein the depression comprises major depressive disorder, persistent depressive disorder, depression associated with bipolar disease, seasonal affective disorder, psychotic depression, postpartum depression, premenstrual dysphoric disorder, situational depression, anhedonia, melancholy, mid-life depression, late-life depression, depression due to identifiable stressors, treatment resistant depression, or combinations thereof.

Aspect 32. The method of aspect 31, wherein the depression is major depressive disorder.

Aspect 33. The method of aspect 32, wherein the major depressive disorder is with melancholic features or anxious distress.

EXAMPLES

Example 1

This example was performed to determine the plasma pharmacokinetic (PK) and bioavailability of a solid dose formulation of [5(4,6-dimethyl-pyrimidin-2-yl)-hexahydro-pyrrolo[3,4-c]pyrrol-2-yl]-(2-fluoro-2-[1,2,3]triazol-2-yl-phenyl)-methanone (Compound A) after single dose tablet administration relative to a suspension formulation. Also addressed are the effect of a semi-fasted condition on the rate and extent of bioavailability of the solid dose formulation and tolerability of the solid and oral suspension formulations.

(i) Reagents and Testing Parameters

[5(4,6-Dimethyl-pyrimidin-2-yl)-hexahydro-pyrrolo[3,4-c]pyrrol-2-yl]-(2-fluoro-2-[1,2,3]triazol-2-yl-phenyl)-methanone (Compound A) was prepared as described in method B in Example 107 U.S. Pat. No. 8,653,263 with the exception that the recrystallization was performed using ethanol instead of an ethanol/2-propanol mixture.

The internal standard was isotope labeled [5(4,6-dimethyl-pyrimidin-2-yl)-hexahydro-pyrrolo[3,4-c]pyrrol-2-yl]-(2-fluoro-2-[1,2,3]triazol-2-yl-phenyl)-methanone which has the following structure.

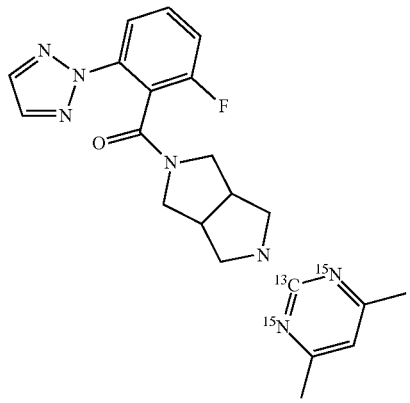

The internal standard was prepared described in method B in Example 107 U.S. Pat. No. 8,653,263 with the exception that step b was performed using isotope labeled Intermediate 92, i.e., 2-(4,6-dimethylpyrimidin-2-yl)octahydropyrrolo[3,4-c]pyrrole, bis-HCl salt, which was prepared using isotope labelled 2-chloro-4,6-dimethyl pyrimidine of the following structure:

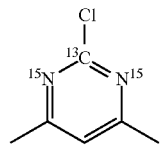

During each treatment period, blood samples were collected for PK measurements. Specifically, venous blood samples of 3 mL each were collected for determination of Compound plasma concentrations. The following plasma Compound A PK parameters were estimated using the actual times of blood sampling:

$C_{max}$ peak plasma concentration.

$t_{max}$ time to reach the peak plasma concentration.

$AUC_{last}$ area under the plasma concentration-time curve from 0 to t hours post study drug dosing, calculated by trapezoidal summation (time t is the time of the last quantifiable concentration $C_{last}$).

$AUC_\infty$ $AUC_{last}$ extrapolated to infinity, calculated as $AUC_{last} + C_{last}/\lambda_z$.

$\lambda_z$ elimination rate constant, determined by linear regression of the terminal points of the ln-linear plasma concentration-time curve.

$t_{1/2}$ terminal half-life, defined as $0.693/\lambda_z$.

CL/F total clearance of drug after extravascular administration, uncorrected for absolute bioavailability, calculated as $Dose/AUC_\infty$.

Vd/F apparent volume of distribution after extravascular administration, uncorrected for absolute bioavailability.

Compound A plasma levels were determined using LC-MS/MS using the equipment and parameters set forth in Tables 1-4.

TABLE 1

| HPLC System | |
|---|---|
| Pump | LC-10 Advp (Shimadzu) with SCL-10 Avp system controller and DGI-14A on-line degasser |
| Pressure limits (psi) | 0-3500 |
| Pumping Mode | Binary |
| Total Flow (mL/min) | 0.350 |
| Initial pump B conc. (%) | 20.0 |
| Column heater | Shimadzu CTO10ACvp |
| Oven temperature (° C.) | 30.0 |
| Autosampler | SIL HTc (Shimadzu) |
| Injection Volume (μL) | 2.00 |
| Cooler Temperature (° C.) | 4 |
| Shimadzu SIL-HTc Properties | |
| Rinsing Volume (μL) | 500 |
| Needle Stroke (mm) | 47 |
| Rinsing Speed (μL/s) | 35 |
| Sampling Speed (μL/s) | 5.0 |
| Purge Time (min) | 1.0 |
| Rinse Dip Time (sec) | 5 |
| Rinse mode | Before and after aspiration |

| Gradient | | | |
|---|---|---|---|
| Time (min) | Module | Events | Parameter |
| 1.50 | Pumps | Pump B Conc. | 50 |
| 1.51 | Pumps | Pump B Conc. | 90 |

TABLE 1-continued

| 2.50 | Pumps | Pump B Conc. | 90 |
| 2.51 | Pumps | Pump B Conc. | 20 |
| 3.00 | Controller | Stop | |

TABLE 2

| Detector | |
| --- | --- |
| Detector | Mass spectrometer API 4000 (AB Sciex) |
| Ion Source | Turbo-ion spray |
| Duration (min) | 4.00 |
| Polarity | Positive MRM |
| Resolution Q1 | unit |
| Resolution Q3 | unit |
| Intensity threshold (cps) | 0.00 |
| CUR | 30.0 |
| CAD | 5.00 |
| GAS 1 (psi) | 40.0 |
| GAS 2 (psi) | 50.0 |
| IS (V) | 5000 |
| Temperature (° C.) | 600 |
| Ihe | On |

TABLE 3

Mass Dependent Parameters

| Compound | Q1 Mass | Q3 Mass | DP (V) | CE (V) | CXP (V) | Time (ms) |
| --- | --- | --- | --- | --- | --- | --- |
| Compound A | 408.2 | 190.0 | 80 | 39 | 13 | 300 |
| Internal Standard Compound B | 411.2 | 190.0 | 80 | 39 | 13 | 300 |

TABLE 4

Blank Matrix

| Matrix | Species | Anti-coagulant |
| --- | --- | --- |
| Plasma | Human | EDTA |
| Analytical column | XBridge BEH C18 column | |
| Dimensions (mm) | 50 × 2.1 | |
| Particle Size (μm) | 3.5 | |
| Typical backpressure | 1500 | |
| Pre-column/filter | Frit filter | |
| HPLC Reagents | | |
| Mobile phase A | 0.1% formic acid in water Mix formic acid (2.00 mL) with water (2000 mL) | |
| Mobile phase B | acetonitrile | |
| Rinse Solvent | 2-propanol:acetonitrile:water:formic acid (40:40:20:0.1v v/v/v/v) Mix propanol (400 mL) with acetonitrile (400 mL) with water (200 mL) and formic acid (1 mL) | |
| Dilution Solvent | 0.1% formic acid in water Mix formic acid (1.00 mL) with water (1000 mL) | |
| Stock Dilution Solvent | dimethylsulfoxide:acetonitrile (50:50, v/v) Mix dimethylsulfoxide (50.0 mL) with acetonitrile (50.0 mL) | |
| System Check Dilution Solvent | 0.1% formic acid in water:acetonitrile (80:20, v/v) Mix 0.1% formic acid (80.0 mL) in water with acetonitrile (20.0 mL) | |

Two stock solutions were prepared for Compound A and one stock solution for internal standard Compound B according to the following.

Compound A Stock Solution: this solution was prepared by dissolving Compound A (1.00 mg) in the Stock Dilution Solvent (10.0 mL)

Compound A Overcurve Stock Solution: this solution was prepared by dissolving Compound A (2.00 mg) in 2.00 mL of the Stock Dilution Solvent (2.00 mL)

Compound B Stock Solution: this solution was prepared by dissolving Compound B (1.00 mg) in 10.0 mL of the Stock Dilution Solvent (2.00 mL).

Standard stock solutions were prepared for Compound A and the internal reference according to the following.

Compound A standard solution 1 (10.0 μg/mL): Compound A Stock Solution (1000 μL) was combined with the Stock Dilution Solvent (10.0 mL).

Compound A standard solution 2 (1.00 μg/mL): Compound A Stock Solution (100 μL) was combined with the Stock Dilution Solvent (10.0 mL).

Compound A Standard Solution 3 (0.100 μg/mL): Compound A Stock Solution (10.0 μL) was combined with the Stock Dilution Solvent (10.0 mL).

Compound B Working Solution (200 mg/mL): Compound B Stock Solution (200 μL) was combined with the Stock Dilution Solvent (100 mL).

Samples were prepared for testing using the following protocol:

(i) Plasma samples at room temperature were homogenized.

(ii) The samples were centrifuged for 5 minutes at about 2500×g and 20° C.

(iii) The plasma sample (50.0 μL) was pipetted into a 1.2 mL round well collection plate.

(iv) Stock Dilution Solvent (50.0 μL) was added to the blanks and the internal standard working solution was added to all other tube. Tubes were then vortexed for 10 seconds.

(v) Acetonitrile (100 μL) was added to each tube and the tubes again vortex-mixed for 10 seconds.

(vi) Acetonitrile (250 μL) was further added to each tube and the tubes again vortex-mixed for 60 seconds.

(vii) The samples were centrifuged for 5 minutes at about 2500×g and 20° C.

(viii) The supernatant (50.0 μL) was transferred into a 1.2 mL round well collection plate using the liquidator.

(ix) Formic acid (0.1%; 400 μL) in water was added to each tube and the tubes vortex-mixed for 10 seconds.

Plots of the chromatograms and peak area integrations were carried out by Analyst (version 1.6.2, MDS Sciex, Concord, Canada). Calculations were done using Watson 7.3 bioanalytical LIMS (Thermo Fisher Scientific).

(ii) Drug Compositions

The suspension containing Compound A was prepared by reconstituting a powder (100 mg Compound A) with hypromellose (5 mg/mL) solution to provide an oral 5 mg/mL oral suspension of Compound A. The hypromellose used for reconstitution is a 0.5% hypromellose solution in sterile water for injection.

The specific procedure for preparing the suspension follows:

(i) A powder containing Compound A is was added to a vial.

(ii) To achieve the desired concentration of the suspension, an appropriate amount of 0.5% HPMC solution was added to the vial.

(iii) A clean stir bar was added to the vial.

(iv) Since it was necessary to suspend the drug substance, the vial with spin bar was placed on a magnetic stir plate and the speed was adjusted to gently create a vortex in the liquid. Once a gentle vortex was achieved, the speed of the stir bar was increased for a rapid vortex at 2500 RPM (about 2400 to about 2600).

(v) The composition was mixed for a minimum of about 24 to about 36 hours.

(vi) After mixing, the suspension was ready for use and the required volume was withdrawn for dosing.

Tablets containing Compound A contained the components set forth in Table 5.

TABLE 5

| Component | Quantity/Unit Dose | |
|---|---|---|
| | (in mg/tablet) | (in % w/w) |
| Compound A | 20 | 13.3 |
| Lactose monohydrate | 80 | 53.3 |
| Microcrystalline cellulose | 40.5 | 27 |
| Crospovidone | 7.5 | 5 |
| Silica colloidal | 1 | 0.7 |
| Magnesium stearate | 1 | 0.7 |
| Total | 150 | 100 |

Figure 16:
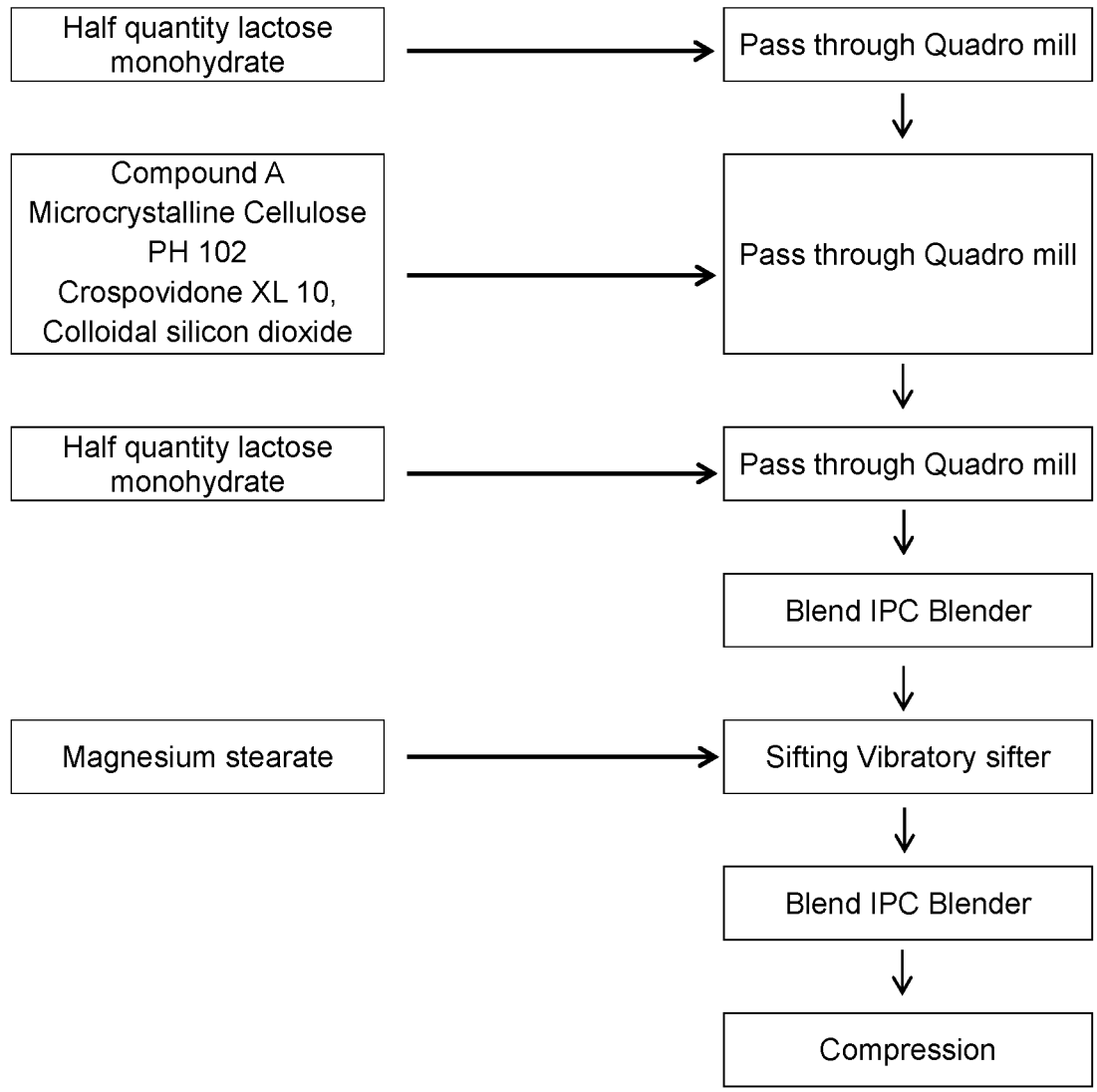
FIG. 16 is the process flow chart regarding the preparation of the tablets used herein.

The tablets were prepared as described in FIG. 16 and according to the following direct compression process:

A. Screening & Blending

1. All materials were passed through a Quadro Comil using 07L039R03125 screen at 1000 rpm, with the exception of magnesium stearate. The following sequence of adding materials to the screen was followed:
   (i) About ½ of the lactose monohydrate
   (ii) Compound A
   (iii) Colloidal Silicon dioxide
   (iv) Crospovidone
   (v) Microcrystalline Cellulose
   (vi) About half of the lactose monohydrate
2. The mixture was blended for 20 minutes at 20 rpm.
3. Magnesium stearate was sifted through a #40 sieve.
4. The mixture of step 3 was blended for 5 minutes at 20 rpm.

B. Compression

The tablets were compressed using a rotary press fitted with a "D" type 7.0 mm round shallow concave punches and appropriate dies. The in-process parameters are set forth in Table 6.

TABLE 6

| Tablet Parameters | Limits |
|---|---|
| Description | White to off white circular biconvex tablets, plain on both sides |
| Friability | not more than (NMT) 1.0% |
| Hardness | 5.0-13.0 kp (target 8.0 kp) |
| Disintegration Time | NMT 15 minutes |
| Individual tablet weight variation | 150 mg ± 7.5% (139.0-161.0 mg) |
| Group Weight of 10 tablets | 1.5 g ± 5% (1.425 g-1.575 g) |
| Thickness | 3.35 mm-3.75 mm (target 3.50 mm) |

(iii) Measurement of PK Parameters

Eighteen male subjects between 18 and 55 years of age, inclusive, were tested. The subjects had not received a potent cytochrome P450(CYP)3A and CYP2C19 inhibitor within 14 days or a period less than 5 times the drug's half-life (whichever was longer) or a potent CYP3A or CYP2C19 inducer within 30 days before study drug administration on Day 1 of Period 1 were excluded.

Subjects received a single oral dose of 20 mg Compound A (suspension or as a solid dose formulation) on Day 1 of each of the 3 treatment periods. The total study duration for each subject (including screening and follow-up visit) was to be about 7 to 8 weeks.

This study consisted of 3 phases: an eligibility screening examination (between 21 days and 2 days prior to first dose administration), a 3-way crossover single dose open-label treatment phase which consisted of 3 treatment periods separated by a washout period of at least 6 days between dosing, and a follow-up visit (within 7 to 14 days after last dose administration).

All subjects enrolled were randomly assigned to one of three Treatments:

Treatment A: 20 mg oral suspension formulation of Compound A (fasted state)

Treatment B: 20 mg solid formulation of Compound A (fasted state)

Treatment C: 20 mg solid formulation of Compound A (semi-fasted state)

(iii) Results

A mixed-effect model was applied to the natural log transformed $C_{max}$ and AUC. The model included sequence, period, treatment as fixed effects, and subject as a random effect. For each of the parameters, the comparisons included:

The solid dosage formulation (fasted) vs. the oral suspension formulation (fasted)

The solid dosage formulation (fasted) vs. the solid dosage formulation (semi-fasted)

Following oral administration, Compound A was rapidly absorbed and reached $C_{max}$ with median $t_{max}$ values ranging from 0.5 to 1.0 hour. Following $C_{max}$, Compound A concentrations declined rapidly in a mono-exponential manner (up to 12 hour postdose). Mean $t_{1/2}$ values for the suspension (fasted) and tablet (semi-fasted) were similar (~2 hours). However, mean $t_{1/2}$ value for the tablet under fasting condition was longer than expected (~5 hours). Extended low levels of plasma concentrations during the terminal phase were found in some subjects resulting in $t_{1/2}$ values ranging from 1.9 to 17.3 hours. See, FIGS. 1-11.

Example 2

This example was performed as a multi-center, double-blind, diphenhydramine and placebo-controlled study. Men and women with a diagnosis of MDD between the ages of 18 and 64, inclusive, were enrolled. At screening, the subjects had a total score of ≥30 on the IDS-$C_{30}$, corresponding to moderate to severe depression.

Blood and saliva were collected for the assessment of biomarkers, among others. Venous blood samples (3 mL each) were collected in fasting condition between 8:00 and 10:00 am for the determination of [5(4,6-dimethyl-pyrimidin-2-yl)-hexahydro-pyrrolo[3,4-c]pyrrol-2-yl]-(2-fluoro-2-[1,2,3]triazol-2-yl-phenyl)-methanone plasma concentrations and biomarkers related to immune system activity, Hypothalamus pituitary adrenal (HPA) axis activation, neurotropic factors and metabolic factors were measured. Pharmacokinetic (PK) blood samples also were collected. Plasma samples were analyzed to determine concentrations of Compound A using LC-MS/MS. Saliva was collected for the measurement of concentrations of cortisol. Saliva concentrations of cortisol were added as a biomarker.

Forty-eight subjects were randomly assigned (in a 2:1:1 ratio) to 20 mg of Compound A, 25 mg diphenhydramine or placebo q.d. (once daily) in the evening over 10 days for women of child bearing potential (WOCBP) or 4 weeks for males and women of non-child bearing potential (WON-CBP). The subjects received the medication as capsules containing 1 tablet of 20 mg Compound A, 1 tablet of 25 mg diphenhydramine or placebo. Males and WONCBP took 1 capsule every evening just before bedtime from Day 1 to Day 28. WOCBP took 1 capsule every evening just before bedtime from Day 1 to Day 10. There were 2 follow up visits occurring at 3 and 14 days.

For the evaluation of symptoms of depression, assessments were done at screening and during the study. Specifically, symptoms of depression were performed using the Mini International Neuropsychiatric Interview (MINI) 6.0 interview, or Hamilton rating scale for Depression-17 (HDRS17). Also, polysomnography (PSG) was performed to quantify sleep stages including latency to persistent sleep (LSP) and total sleep time (TST). Thereafter, symptoms of depression were taking on days 11 and 29 during treatment and days 3 and 14 following treatment. PSG was recorded overnight after the first and tenth dose administration of study medication.

(i) Posology

Compound A was found to be an orally active, selective antagonist of the orexin-2 receptor. After oral administration of 20 mg, Compound A had a short time to maximal plasma concentrations ($T_{max}$<1 hour) and was characterized by a short half-life (2-3 hours). Daytime administration of Compound A induced somnolence in healthy subjects while nighttime administration reduced the latency to persistent sleep (LPS) and prolongs the total sleep time (TST) in subjects with insomnia disorder (ID). The magnitude of the effect of Compound A on LPS and TST is directly related to level of insomnia at baseline. See, FIGS. 12-15.

Nighttime administration (within 30 minutes before bedtime) resulted in intermittent exposure of Compound A to plasma. Thus, it was demonstrated that repeated (10 days) daily dose administration did not result in accumulation.

(ii) $HDRS_{17}$/HAM-$D_6$

A $HDRS_{17}$ total score was calculated by summing the 17 item scores taken during the study. A $HDRS_{17}$ total score ranges from 0 to 52, with higher scores indicating greater severity of depression. In order to correct for a possible effect of study medication on sleep, sleep-related items were removed from the $HDRS_{17}$ to calculate a (sleep item)-adjusted HDRS. Accordingly, an adjusted $HDRS_{17}$ total score was calculated by summing the item scores excluding the 3 insomnia questions (4-Insomnia Early, 5-Insomnia Middle and 6-Insomnia Late). A $HDRS_{17}$ adjusted total score ranges from 0 to 46. A 6-item subscale from the HDRS17 (HAM-$D_6$) was analyzed and provided information to core depressive symptoms and is sensitive to treatment response. The six items included depressed mood, guilt feelings, work and interests, psychomotor retardation, psychic anxiety, and general somatics (tiredness and pains).

TABLE 7

| | | Mean score ± standard deviation | | |
| | | | Compound | |
| Study | Time | Placebo (N = 12) | Compound A 20 mg (N = 22) | Diphenhydramine 25 mg (N = 13) |
| --- | --- | --- | --- | --- |
| Total $HDRS_{17}$ | Baseline | 18.7 (5.71) | 18.7 (4.65) | 20.0 (5.12) |
| | Day 11 Change from baseline | −3.6 (4.03) | −5.5 (3.86) | −4.1 (3.66) |
| Mean Adjusted HDRS17 | Baseline | 13.7 (4.98) | 14.4 (3.36) | 15.1 (4.41) |
| | Day 11 Change from baseline | −2.3 (3.03) | −4.5 (2.76)* | −2.3 (2.81) |

The results in Table 7 illustrate that the improvement in the total $HDRS_{17}$ observed after administration of 20 mg of Compound A is mostly unrelated to changes in sleep (−5.5 versus −4.5 points) whereas sleep-related changes appear to more important for diphenhydramine (−4.1 versus −2.3).

The HAM-$D_6$ score was calculated by summing the 6 items scores, and ranges from 0 to 22. Higher scores indicate greater severity of core symptoms.

TABLE 8

| | | Mean scores ± standard deviation | | |
| | | | Compound | |
| Score | Time | Placebo (N = 12) | Compound A 20 mg (N = 22) | Diphenhydramine 25 mg (N = 13) |
| --- | --- | --- | --- | --- |
| mean $HDRS_{17}$ anxiety/ somatization factor score | Baseline | 4.3 (1.56) | 4.8 (1.56) | 5.1 (1.80) |
| | Day 11 Change from baseline | −0.8 (1.40) | −1.6 (1.50) | −0.9 (1.12) |
| Mean HAM-$D_6$ | Baseline | 9.0 (3.57) | 10.4 (2.09) | 10.6 (3.31) |
| | Day 11 Change from baseline | −1.5 (2.15) | −3.8 (2.22)** | −1.8 (2.01) |

The results in Table 8 illustrate that the change from baseline in the HDRS anxiety/somatization factor did not account for the observed improvement in depression ratings in the Compound A group. However, the core symptoms of depression (per HAM-$D_6$) did account for the observed improvement in depression ratings in the Compound A group.

(iii) Polysomnography

The effects of study medication on polysomnography (PSG)-derived parameters was evaluated overnight on Days 1/2 and 10/11. In addition, PSG was recorded up to and following a forced wake overnight on Day 5/6. Two screening PSG recordings were made and baseline values were calculated as the average values recorded at Screening 1 and 2.

(a) Total Sleep Time (TST)

TST is defined as total minutes spent in rapid eye movement (REM) and non-REM sleep. Compared to placebo, both Compound A and diphenhydramine increased TST overnight on Day 1/2. Because of an increase in TST in placebo-treated subjects on Day 10/11, the relative effect of Compound A and diphenhydramine were less pronounced. See, Table 9. Although the overall study population did not meet criteria for insomnia disorder (TST<360 minutes), individual subjects had baseline TST values as low as 263 minutes. Thus, the population was mixed with respect to the presence of insomnia disorder.

TABLE 9

| Time (min) | Compound | | |
|---|---|---|---|
| | Placebo (N = 12) | Compound A 20 mg (N = 22) | Diphenhydramine 25 mg (N = 13) |
| Baseline | 376 (56.2) | 380 (50.1) | 382 (47.2) |
| Day 1/2 Change from baseline | 7.4 (52.07) | 30.9 (54.06) | 28.3 (33.92) |
| Day 10/11 Change from baseline | 20.7 (64.44) | 26.56 (56.11) | 33.92 (46.01) |

Figure 13:
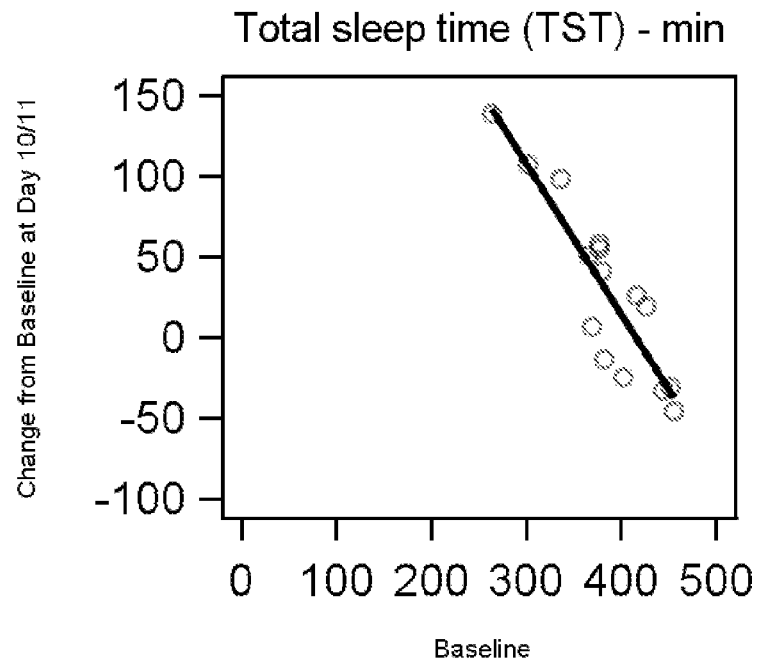
FIG. 13 is a line graph of the time (min) of total sleep vs. the change from baseline at day 10/11.
Figure 14:
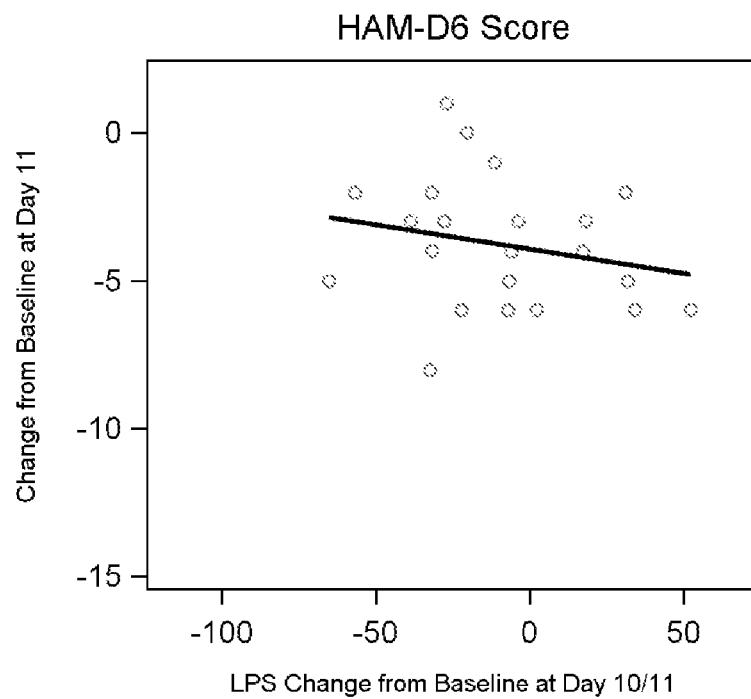
FIG. 14 is a line graph of the latency to persistent sleep (LPS) change in Hamilton Depression Rating Scale (HAM-$D_6$) score from baseline at day 10/11 vs. the HAM-$D_6$ change from baseline at day 11.
Figure 15:
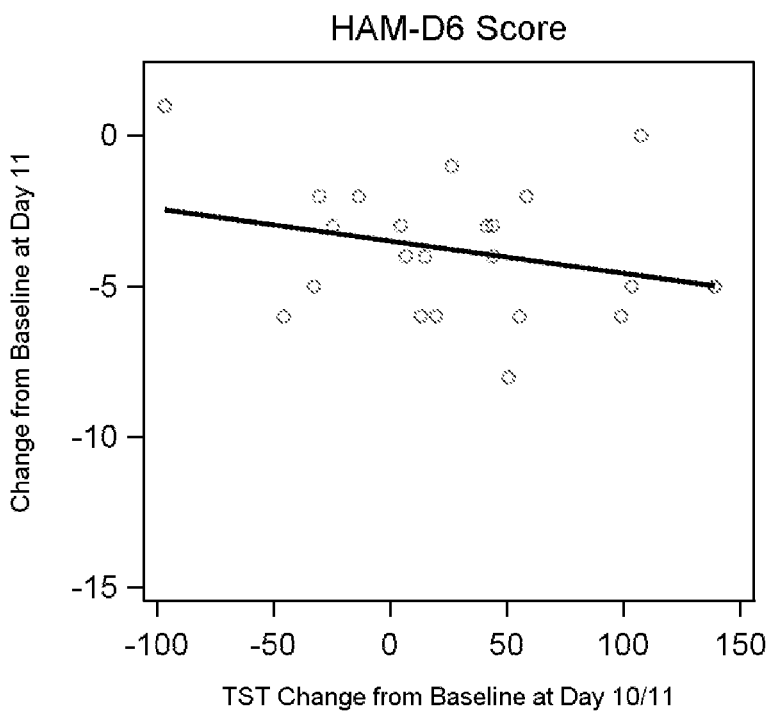
FIG. 15 is a line graph of the total sleep time (TST) change in HAM-$D_6$ score from baseline at day 10/11 vs. the HAM-$D_6$ score change from baseline at day 11.

The effect of Compound A on TST is proportional to the TST duration at baseline (FIG. 13). However, no relationship between the magnitude of the LPS change and the improvement in core depressive symptoms was observed (FIG. 15) supporting an antidepressant effect independent from an effect on insomnia.

(b) Latency to Persistent Sleep

LPS is defined as the elapsed time (in minutes) from lights out to 10 minutes of continuous sleep. Compared to placebo, both Compound A and diphenhydramine modestly reduced LPS overnight on Day 1/2. Because of a decrease in LPS in placebo-treated subjects overnight on Day 10/11, the relative effect of Compound A and diphenhydramine were less pronounced. See, Table 10. Overall, the study population was characterized by a prolonged (>20 minutes) LPS. Similar as for TST, the population was mixed with respect to the presence of insomnia disorders at baseline with LPS values as low as 4.5 minutes.

TABLE 10

| Time (min) | Compound | | |
|---|---|---|---|
| | Placebo (N = 12) | Compound A 20 mg (N = 22) | Diphenhydramine 25 mg (N = 13) |
| Baseline | 53.8 (40.12) | 40.9 (22.62) | 36.0 (19.20) |
| Day 1/2 Change from baseline | 3.4 (46.39) | 8.7 (36.04) | 6.7 (26.40) |
| Day 10/11 Change from baseline | 17.5 (51.40) | 9.2 (30.41) | 0.3 (30.57) |

Figure 12:
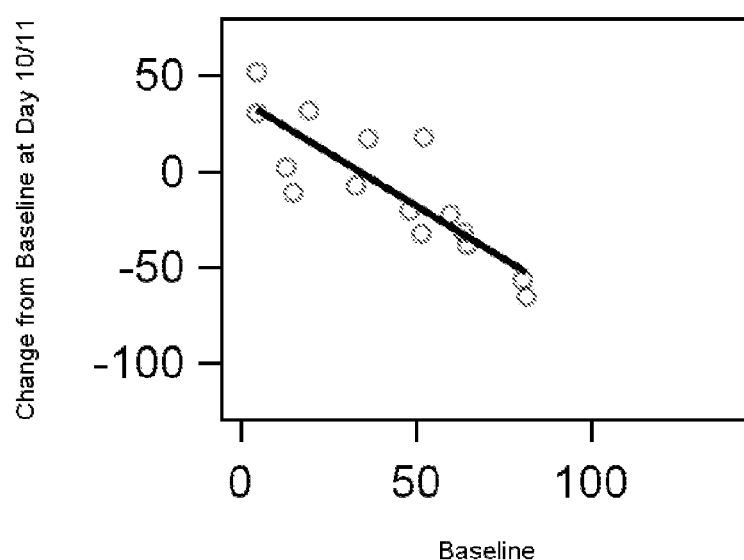
FIG. 12 is a line graph of the time (min) from lights out to 10 minutes of sleep vs. the change from baseline at day 10/11.

The effect of Compound A on LPS is proportional to the LPS duration at baseline (FIG. 12). However, no relationship between the magnitude of the LPS change and the improvement in core depressive symptoms was observed (FIG. 14) supporting an antidepressant effect independent from an effect on insomnia.

(iv) Summary

These results show that, compared to placebo and diphenhydramine, the antidepressant effect of Compound A was larger and clinically relevant. Surprisingly, the effect of Compound A was largely related to an effect on the core symptoms of depression and overall unrelated to its effect on sleep related items. The antidepressant effect was sustained at least 14 days after treatment discontinuation. Of importance, improvements were already observed on Day 11 (first assessment) and were sustained upon treatment discontinuation.

Example 3

This example was performed to illustrate that Compound A may be used in an adjunctive therapy. Specifically, Compound A was administered to subjects diagnosed with MDD (i) as a monotherapy and (ii) in combination with a known anti-depressant and the symptoms of depression of the subjects evaluated using the HDRS17 and HAM-$D_6$ scale In Group 1, thirty seven subjects were randomly assigned (in a 2:1:1 ratio) to 20 mg of Compound A, 25 mg diphenhydramine or placebo q.d. in the evening over 10 days. In Group 2, ten subjects were randomly assigned (in a 2:1:1 ratio) to 20 mg of Compound A, 25 mg diphenhydramine or placebo q.d. in the evening over 10 days. Each subject in Group 2 also took an amount of antidepressant selected from duloxetine, citalopram, paroxetine, or sertraline and as prescribed by their attending physician. For the evaluation of symptoms of depression for both groups, assessments were independently performed at screening and on Day 11, i.e., one day after the study, using $HDRS_{17}$ and HAM-$D_6$ as described in Example 2. The results of the evaluations are summarized in Tables 11 and 12. In Tables 11-12, # denotes the Cohen effect size, * denotes P<0.05 (statistically significant), and ** denotes P<0.01.

TABLE 11

| | | Mean scores ± SD Group I | | |
|---|---|---|---|---|
| Scale | Time | Placebo (N = 8) | Compound A 20 mg (N = 18) | Diphenhydramine 25 mg (N = 11) |
| HDRS17 | Baseline | 19.5 (5.40) | 19.4 (4.80) | 21.5 (3.78) |
| | Day 11 Change from baseline | −2.5 (4.14) | −5.1 (3.97) | −4.2 (4.00) |
| | Effect Size Compound A vs Placebo# | | −0.64 | |
| Adjusted HDRS | Baseline | 14.4 (4.50) | 14.9 (3.37) | 16.4 (3.35) |
| | Day 11 Change from baseline | −1.4 (3.29) | −4.3 (2.97)* | −2.1 (3.02) |
| | Effect Size Compound A vs Placebo# | | −0.93 | |
| Anxiety-Somatization Factor | Baseline | 4.4 (1.41) | 5.1 (1.53) | 5.5 (1.51) |
| | Day 11 Change from baseline | −0.8 (1.49) | −1.6 (1.65) | −0.8 (1.17) |
| | Effect Size Compound A vs Placebo# | | −0.51 | |
| HAM-D$_6$ | Baseline | 9.6 (3.70) | 10.8 (2.07) | 11.7 (2.05) |
| | Day 11 Change from baseline | −0.8 (2.25) | −3.6 (2.33)** | −1.7 (2.15) |
| | Effect Size Compound A vs Placebo# | | −1.22 | |

TABLE 12

| | | Group 2 | | |
|---|---|---|---|---|
| | | Placebo (N = 4) | Compound A 20 mg (N = 4) | Diphenhydramine 25 mg (N = 2) |
| HDRS17 | Baseline | 17.0 (6.78) | 15.5 (2.08) | 11.5 (0.71) |
| | Day 11 Change from baseline | −5.8 (3.20) | −7.0 (3.37) | −3.5 (0.71) |
| | Effect Size Compound A vs Placebo# | | −0.37 | |
| Adjusted HDRS | Baseline | 12.3 (6.29) | 11.8 (1.89) | 8.0 (1.41) |
| | Day 11 Change from baseline | −4.3 (0.96) | −5.5 (1.29) | −3.5 (0.71) |
| | Effect Size Compound A vs Placebo# | | −1.06 | |
| Anxiety-Somatization Factor | Baseline | 4.3 (2.06) | 3.5 (1.00) | 2.5 (0.71) |
| | Day 11 Change from baseline | −1.0 (1.41) | −1.8 (0.50) | −1.5 (0.71) |
| | Effect Size Compound A vs Placebo# | | −0.76 | |
| HAM-D$_6$ | Baseline | 7.8 (3.40) | 8.8 (1.26) | 4.5 (0.71) |
| | Day 11 Change from baseline | −3.0 (0.82) | −4.8 (1.50) | −2.0 (1.41) |
| | Effect Size Compound A vs Placebo# | | −1.49 | |

These results illustrate that Compound A has antidepressant efficacy in untreated and antidepressant drug-treated subjects with MDD supporting its efficacy as monotherapy and adjunctive therapy.

The disclosures of each patent, patent application, and publication cited or described in this document are hereby incorporated herein by reference, in its entirety.

Those skilled in the art will appreciate that numerous changes and modifications can be made to the preferred embodiments of the disclosure and that such changes and modifications can be made without departing from the spirit of the disclosure. It is, therefore, intended that the appended claims cover all such equivalent variations as fall within the true spirit and scope of the disclosure.

What is claimed is:

1. A method of treating depression associated with bipolar disorder in a subject, comprising administering to the subject in need of such treatment an effective amount of a compound of formula (I):

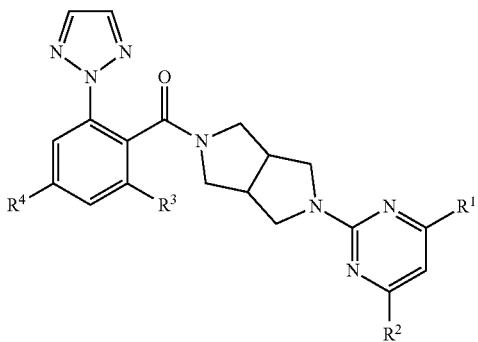

wherein:
$R^1$ is $C_{1-4}$ alkyl;
$R^2$ is $C_{1-4}$ alkyl;
$R^3$ is H or halogen; and
$R^4$ is H or $C_{1-4}$ alkoxy:
or a pharmaceutically acceptable salt or hydrate thereof.

2. The method of claim 1, wherein the subject is not suffering from or diagnosed with an insomnia disorder.

3. The method of claim 1, wherein $R^3$ is halogen.

4. The method of claim 1, wherein $R^4$ is H.

5. The method of claim 1, wherein the compound is [5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone or a pharmaceutically acceptable salt thereof.

6. The method of claim 1, wherein the compound is [5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone.

7. The method of claim 1, wherein the compound is [5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone hydrochloride.

8. The method of claim 1, wherein the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone or a pharmaceutically acceptable salt thereof.

9. The method of claim 1, wherein the compound is (5-(4,6-dimethylpyrimidin-2-yl)hexahydropyrrolo[3,4-c]pyrrol-2(1H)-yl)(4-methoxy-2-(2H-1,2,3-triazol-2-yl)phenyl)methanone.

10. The method of claim 5, wherein the effective amount of the compound is about 10 to about 40 mg.

11. The method of claim 10, wherein the compound is administered once daily.

12. The method of claim 11, wherein the compound is administered at night.

13. The method of claim 11, wherein the compound is administered prior to sleep.

14. The method of claim 12, wherein the compound is administered prior to sleep.

15. The method of claim 5, wherein the effective amount of the compound is about 20 mg.

16. The method of claim 15, wherein the compound is administered once daily.

17. The method of claim 16, wherein the compound is administered at night.

18. The method of claim 16, wherein the compound is administered prior to sleep.

19. The method of claim 17, wherein the compound is administered prior to sleep.

20. The method of claim 5, wherein the compound is administered as an adjunctive treatment.

21. The method of claim 20, wherein the effective amount of the compound is about 10 to about 40 mg.

22. The method of claim 21, wherein the compound is administered once daily.

23. The method of claim 22, wherein the compound is administered at night.

24. The method of claim 22, wherein the compound is administered prior to sleep.

25. The method of claim 23, wherein the compound is administered prior to sleep.

26. The method of claim 20, wherein the effective amount of the compound is about 20 mg.

27. The method of claim 26, wherein the compound is administered once daily.

28. The method of claim 27, wherein the compound is administered at night.

29. The method of claim 27, wherein the compound is administered prior to sleep.

30. The method of claim 28, wherein the compound is administered prior to sleep.

* * * * *